US005730714A

United States Patent [19]
Guy et al.

[11] Patent Number: 5,730,714
[45] Date of Patent: *Mar. 24, 1998

[54] METHOD FOR THE IONTOPHORETIC NON-INVASIVE DETERMINATION OF THE IN VIVO CONCENTRATION LEVEL OF GLUCOSE

[75] Inventors: Richard Guy; Girish Rao, both of San Francisco, Calif.; Peretz Glikfeld, Ness-Ziona, Israel; Christopher Cullander, Berkeley, Calif.; Robert S. Hinz, Mill Valley, Calif.

[73] Assignee: The Regents of the University of California, Oakland, Calif.

[*] Notice: The term of this patent shall not extend beyond the expiration date of Pat. No. 5,279,543.

[21] Appl. No.: 312,400

[22] Filed: Sep. 26, 1994

Related U.S. Application Data

[63] Continuation of Ser. No. 771,483, Oct. 4, 1991, Pat. No. 5,362,307, which is a continuation-in-part of Ser. No. 299,397, Jan. 24, 1989, abandoned, which is a continuation-in-part of Ser. No. 150,159, Jan. 29, 1988, abandoned.

[51] Int. Cl.[6] .................................................. A61N 1/30
[52] U.S. Cl. ............................................. 604/20; 128/639
[58] Field of Search ........................... 604/20; 128/639, 128/640, 749, 760, 762, 767; 607/115, 148, 152, 153

[56] References Cited

U.S. PATENT DOCUMENTS

| 4,141,359 | 2/1979 | Jacobsen et al. | 128/172.1 |
|---|---|---|---|
| 4,166,457 | 9/1979 | Jacobsen et al. | 128/639 |
| 4,239,046 | 12/1980 | Ong | 128/640 |
| 4,250,878 | 2/1981 | Jacobsen et al. | 187/207.21 |
| 4,329,999 | 5/1982 | Phillips | 128/760 |

(List continued on next page.)

FOREIGN PATENT DOCUMENTS

| 7769187 | 3/1988 | Australia | A61N 001/44 |
|---|---|---|---|
| 120689 | 10/1984 | European Pat. Off. | A61M 1/00 |
| 230153 | 7/1987 | European Pat. Off. | A61N 1/30 |
| 230749 | 8/1987 | European Pat. Off. | A61N 1/30 |
| 240593 | 10/1987 | European Pat. Off. | A61N 1/30 |

(List continued on next page.)

OTHER PUBLICATIONS

F.B. Benjamin et al (1954) "Sodium–Potassium Ratio in Human Skin as Obtained by Reverse Iontophoresis," Journal of Applied Physiology, Vol. 6, pp. 401–407.

(List continued on next page.)

*Primary Examiner*—John P. Lacyk
*Attorney, Agent, or Firm*—Peters, Verny, Jones & Biksa, L.L.P.

[57] ABSTRACT

The present invention relates to an vitro device for the removal of ionized substances from a membrane sample without mechanical penetration, which device comprises:

(a) a positive electrode;
(b) a negative electrode, and
(c) electrical insulation between subpart (a) and (b), wherein the positive electrode, and the negative electrode, and electrical insulation are positioned on the same side of the membrane sample.

The present invention also relates to a device for the removal of or delivery of ionized substances to a mammal through intact skin or mucosal membrane without mechanical penetration, which device comprises: (a) a positive electrode, (b) a negative electrode, and (c) an electrically insulating material between subpart (a) and (b), wherein the positive electrode, negative electrode and insulating material are physically positioned so that each present a common surface of the device for contact with the same surface of the skin or mucosal membrane of the mammal.

The present invention also relates to the use of iontophoresis to determine the level of a charged molecule in a living mammal, and with the use of a feedback mechanism, administer appropriate levels of therapeutic substances.

23 Claims, 19 Drawing Sheets

U.S. PATENT DOCUMENTS

| | | | |
|---|---|---|---|
| 4,383,529 | 5/1983 | Webster | 604/20 |
| 4,406,658 | 9/1983 | Lattin et al. | 604/20 |
| 4,411,648 | 10/1983 | Davis et al. | 604/21 |
| 4,416,274 | 11/1983 | Jacobsen et al. | 604/20 |
| 4,419,092 | 12/1983 | Jacobsen | 604/20 |
| 4,456,012 | 6/1984 | Lattin | 128/420 R |
| 4,474,570 | 10/1984 | Ariura | 604/20 |
| 4,477,971 | 10/1984 | Jacobsen et al. | 129/877 |
| 4,557,723 | 12/1985 | Sibalis | 604/20 |
| 4,585,652 | 4/1986 | Miller et al. | 424/83 |
| 4,595,011 | 6/1986 | Phillips | 128/636 |
| 4,602,909 | 7/1986 | Csillik et al. | 604/20 |
| 4,622,031 | 11/1986 | Sibalis | 604/20 |
| 4,633,879 | 1/1987 | Ong | 128/641 |
| 4,679,560 | 7/1987 | Galbraith | 128/410 R |
| 4,689,039 | 8/1987 | Masaki | 604/20 |
| 4,693,711 | 9/1987 | Bremer et al. | 604/306 |
| 4,699,146 | 10/1987 | Sieverding | 128/640 |
| 4,700,710 | 10/1987 | Hoffman | 128/641 |
| 4,702,732 | 10/1987 | Powers et al. | 604/20 |
| 4,706,680 | 11/1987 | Keusch | 128/640 |
| 4,708,716 | 11/1987 | Sibalis | 604/20 |
| 4,713,050 | 12/1987 | Sibalis | 604/20 |
| 4,717,378 | 1/1988 | Perrault et al. | 604/20 |
| 4,721,111 | 1/1988 | Muttitt | 128/640 |
| 4,722,354 | 2/1988 | Axelgaard et al. | 128/798 |
| 4,722,726 | 2/1988 | Sanderson et al. | 604/20 |
| 4,727,881 | 3/1988 | Craighead et al. | 128/641 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,756,314 | 7/1988 | Eckenhoff et al. | 128/760 |
| 4,764,164 | 8/1988 | Sasaki | 604/20 |
| 4,767,401 | 8/1988 | Siederman | 604/20 |
| 4,786,277 | 11/1988 | Powers et al. | 604/20 |
| 4,786,278 | 11/1988 | Masaki | 604/20 |
| 4,808,152 | 2/1989 | Sabalis | 604/20 |
| 4,810,699 | 3/1989 | Sabatucci et al. | 514/161 |
| 4,820,263 | 4/1989 | Spevak et al. | 604/20 |
| 4,823,810 | 4/1989 | Dervieux | 128/783 |
| 4,832,036 | 5/1989 | Cartmell | 128/783 |
| 4,842,577 | 6/1989 | Konno et al. | 604/20 |
| 4,848,353 | 7/1989 | Engel | 128/640 |
| 5,279,543 | 1/1994 | Glikfeld et al. | 604/20 |
| 5,362,307 | 11/1994 | Guy et al. | 604/20 |

FOREIGN PATENT DOCUMENTS

| | | | |
|---|---|---|---|
| 252732 | 1/1988 | European Pat. Off. | A61M 37/00 |
| 254965 | 2/1988 | European Pat. Off. | A61N 1/30 |
| 267293 | 5/1988 | European Pat. Off. | A61M 37/00 |
| 278473 | 8/1988 | European Pat. Off. | A61K 37/02 |
| 278474 | 8/1988 | European Pat. Off. | A61M 37/02 |
| 282982 | 9/1988 | European Pat. Off. | A61N 1/30 |
| 293893 | 12/1988 | European Pat. Off. | A61N 1/30 |
| 322098 | 6/1989 | European Pat. Off. | C08F 226/06 |
| 2116850 | 10/1983 | United Kingdom | A61M 1/00 |
| 8607269 | 12/1986 | WIPO | A61N 1/30 |
| 8800846 | 2/1988 | WIPO | A61N 1/30 |

OTHER PUBLICATIONS

J.S. Schultz, "Medical Applications of Fiberoptic Sensors," *Medical Instrumentation*, vol. 19, #4, (Jul.–Aug., 1985), pp. 158–163.

A.P.F. Turner et al., "Commercial perspectives for diagnostics using biosensors technologies," ABL, pp. 10–18, published Nov. 1988.

W. Schramm, et al., "The Commercialization of Biosensors," MD. & DI, pp. 52–57, published Nov. 1987.

A.P.F. Turner, "Diabetes Mellitus, Biosensors for Research and Management," Biosensors, vol. 1, pp. 85–115, publieshed by Elsevier, Ltd., London, U.K.

L.P. Gangarosa et al, Journal of Pharmacology and EXP. Therap. 1980, V. 212, #3, P 377–381.

K. Okabe et al., J. of Controlled Release, V4 1986, pp. 79–85.

U. Sonnhof, Pflugers Arch., V. 341, pp. 351–358 (1973).

A. Arancibia, et al, Il Farmoco–Ed. Pr. V. 40 Facs 11, pp. 388–395.

N.H. Bellantone, et al., Int. J. of Pharmaceutics, V. 30, (1986), pp. 63–72.

H. Pratzel et al., Journal of Rheumatology, V. 13, pp. 1122–1125, (1986).

J. E. Sanderson, et al, J. of Pharmaceutical Sciences, V. 76, #3, Mar. 1987, pp. 215–218.

F. Roberts, Neutropharmacology, V. 20, pp. 711–714, (1981).

L. E. Linblad, et al. Journal of Investigative Dermatology, Inc. Dec. 1986, pp. 634–636.

O. Siddiqui, et al. J. of Pharm. Pharmacology, 1985, V. 37, pp. 732–735.

M.P. Jones et al. Clinical and Experimental Dermatology, 1986, V 11, pp. 54–61.

R. J. Kasser et al, J. of Neuroscience Methods, V. 7, 1983, pp. 235–242.

M. Peltoranta et al., Medical and Biological Eng. and Computing, V. 21, Nov. 1983, pp. 731–738.

P. Tyle, Pparmaceutical Reserearch, v. 3, 36, 1986, pp. 318–326.

J.L. Stauber et al, The Science of the Total Environmen v. 60, 1987, .pp. 263–271.

A, Chantraine et al., Arch. Phys. Ved. Rehabil, V. 67, Jan. 1986, pp. 38–40.

B. Turek et al., Cs. Dermatologie, V 41, #6, pp. 376–379.

C. C. Peck, et al. J. of Pharmacokinetics and Biopharmaceutics, v. 9, #1 1981, pp. 41–58.

J.B. Phipps et al. Iontophoretic Delivery . . . Skins, Medtronic, Inc. Minneapolis, MN. p. 179.

R. T. Johnson, On the Safe Electrical Admin . . . Iontophoresis, 30th ACEMB Mtg. Nov. 5–9, 1977 Los Angeles CA p. 97.

D.L.Craig et al Australian Physical and Eng. Sci in Medicine, 1983, V. 6, #3, pp. 125–127.

P.D. Gadsby M.S. Medical Instrumentation, V. 13, #5, Sep.–Oct. 1979, 281–283.

R. R. Burnette et al, J. of Pharmaceutical Sciences, vo. 75, #8, Aug. 1986, pp. 738–743.

C.C. Peck, et al, Pharmacol. Skin. V. 1, (1987) pp. 201–208.

R. Tapper, J. of Clinical Engineering, V. 8, #3, Jul.–Sep. 1983, p. 2530259.

V. K. Ulaskchik, Zdravookhr. Beloruss., V. 15, #4 , 1969, pp. 41–44.

G.A. Rossi et al. Instituto di Farmacologia, dell 'Universita, Pervenuto in redazione il 2 Febbraio 1983, pp. 806–812.

V.S. Ulashchik et al, Vopr. Kurortol, Fizloter. Lech, Fiz. Ku; 't. (4), pp. 58–62 (1977).

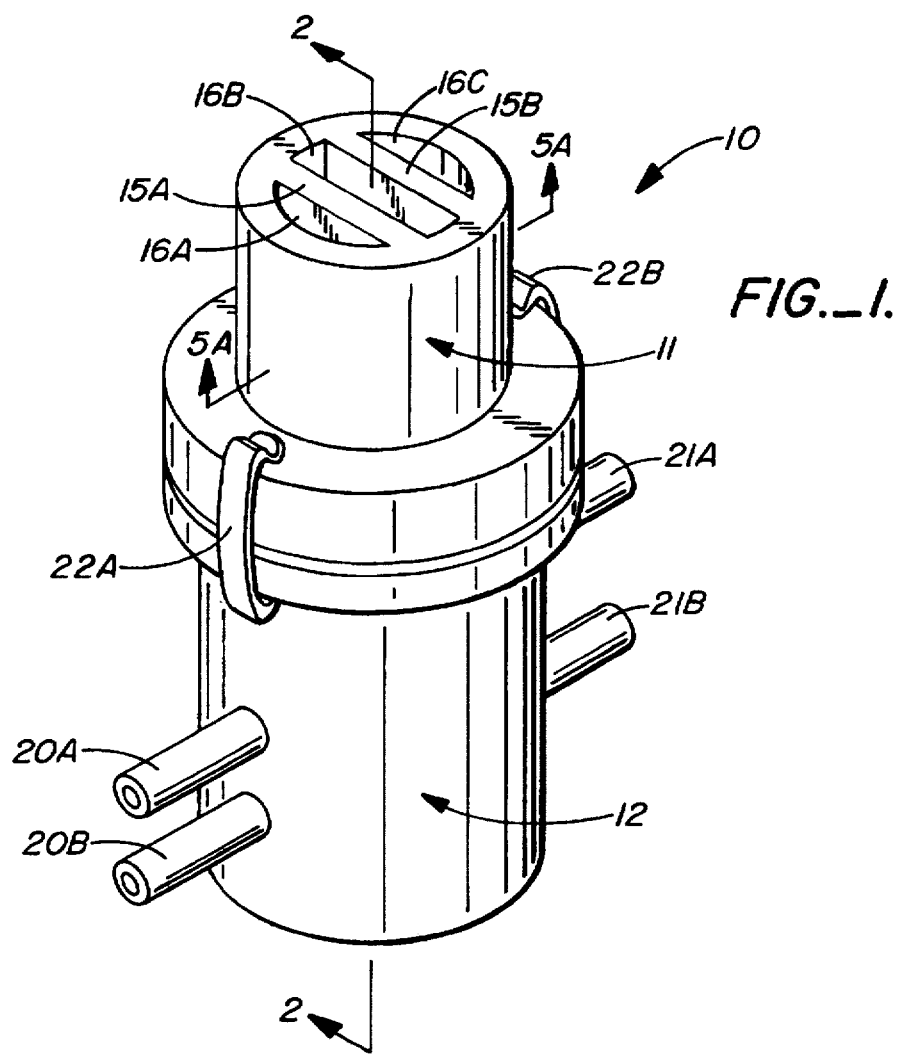
FIG._1.
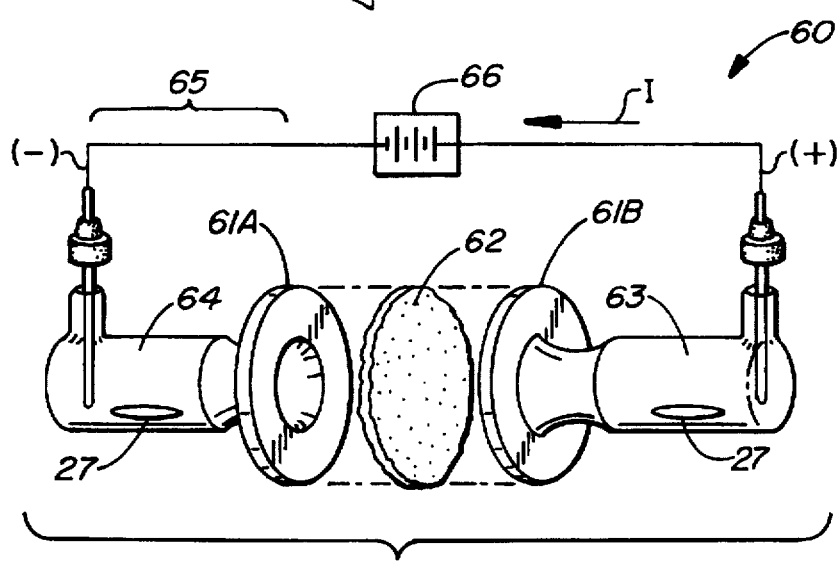
FIG._6. (PRIOR ART)

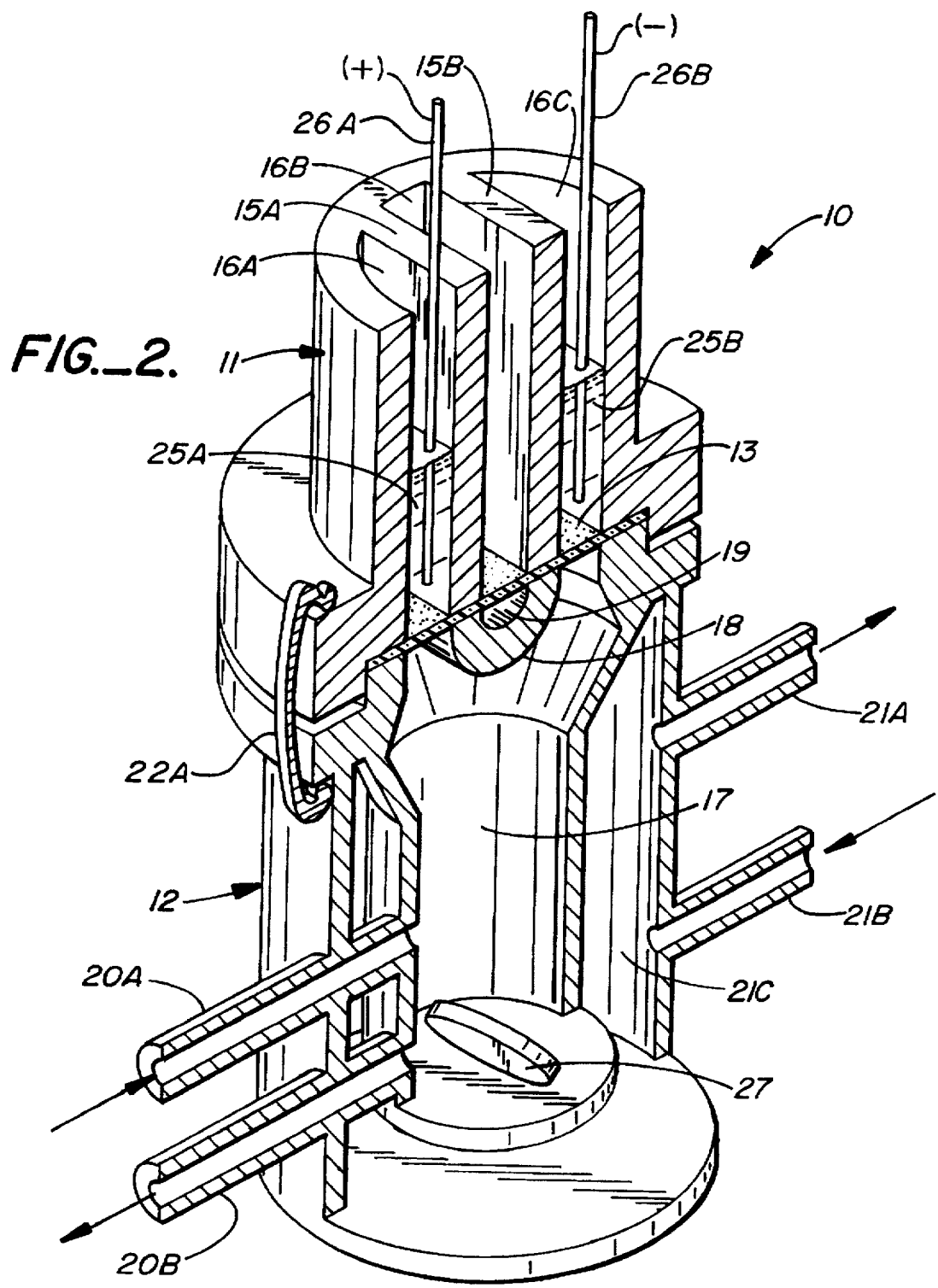
FIG._2.

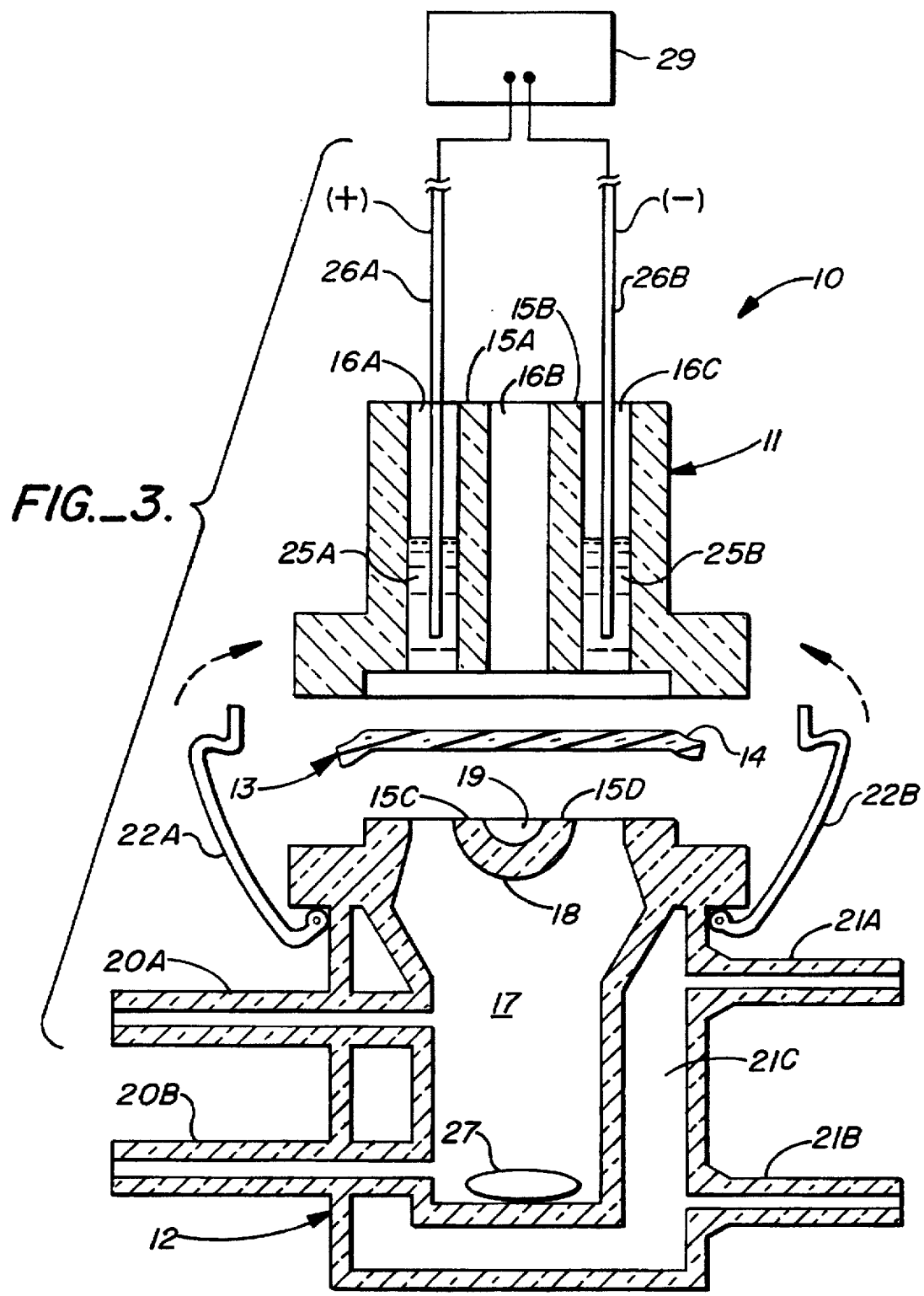
FIG._3.

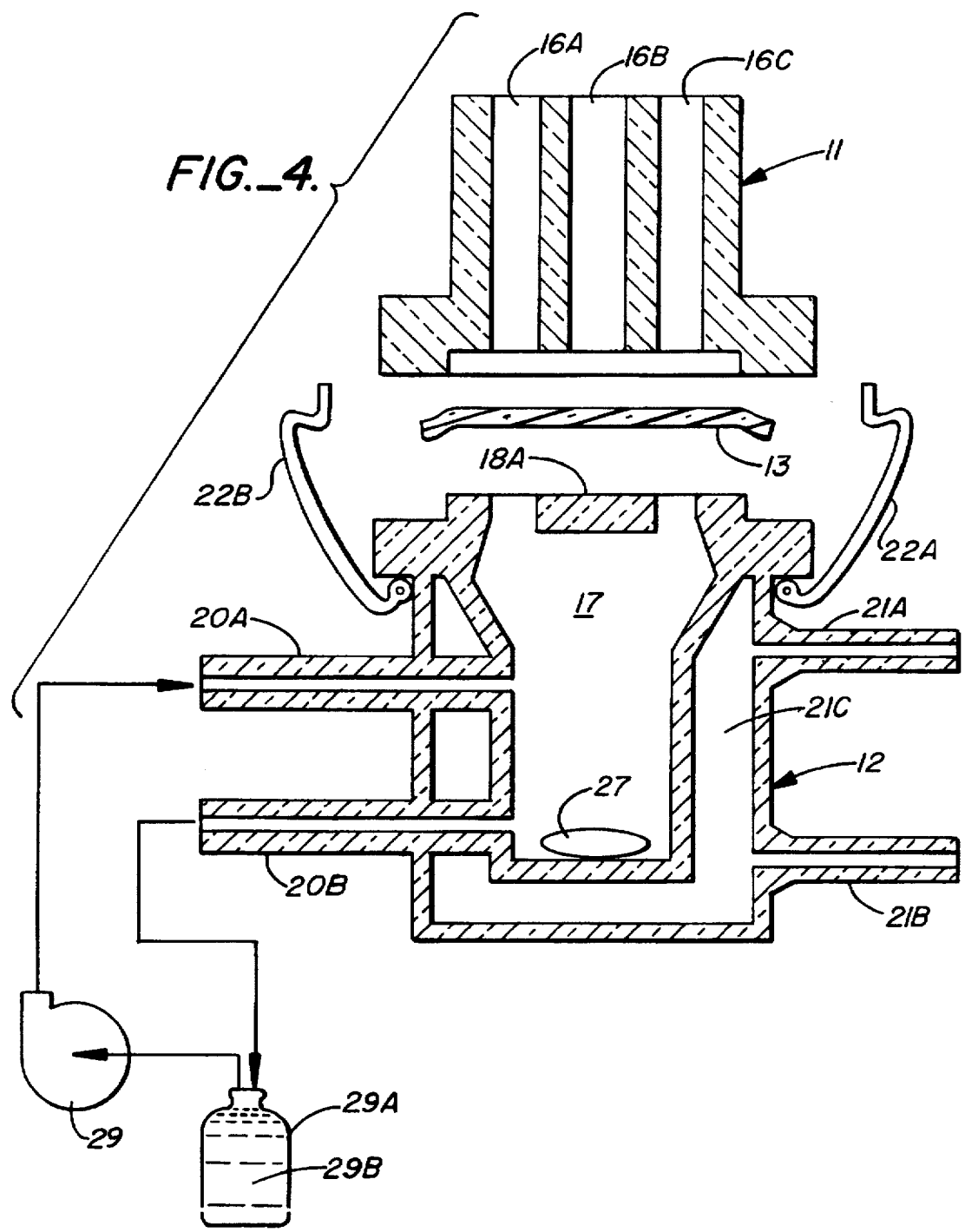
FIG._4.

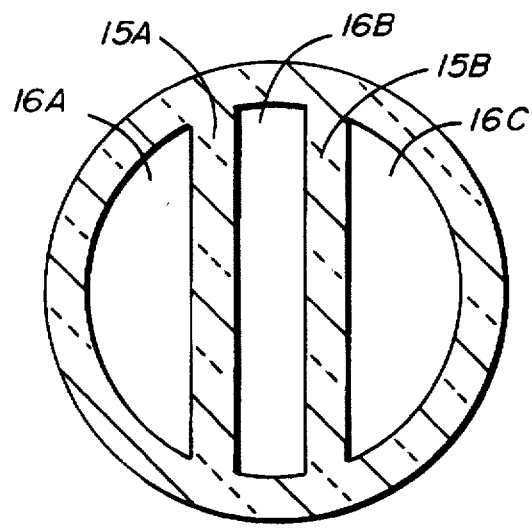
FIG._5A
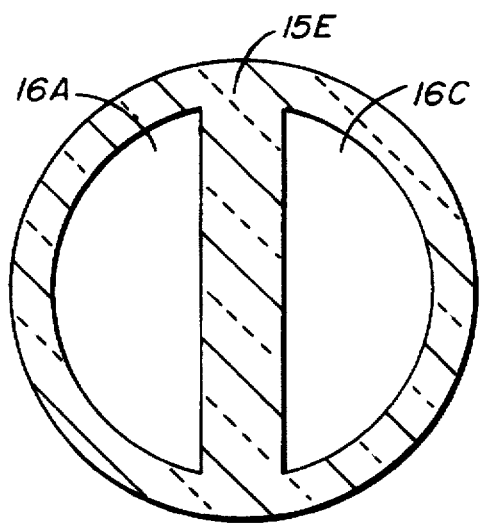
FIG._5B
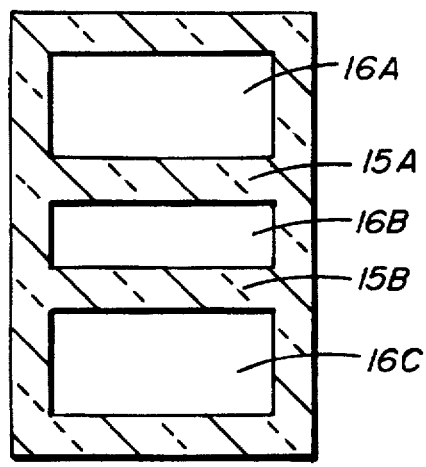
FIG._5C
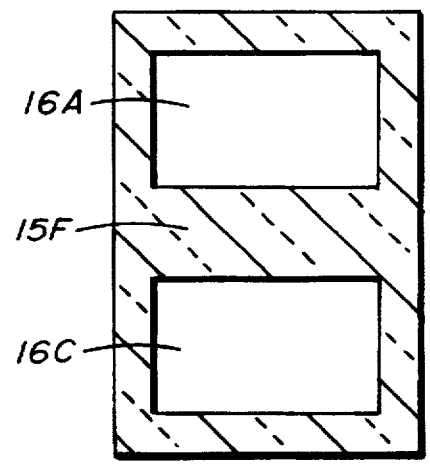
FIG._5D

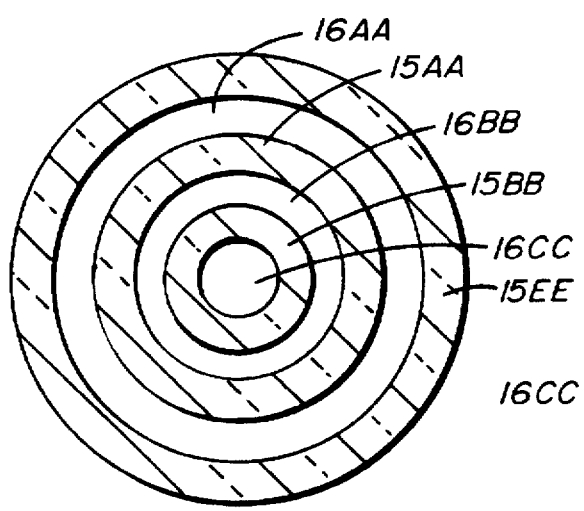
FIG._5E
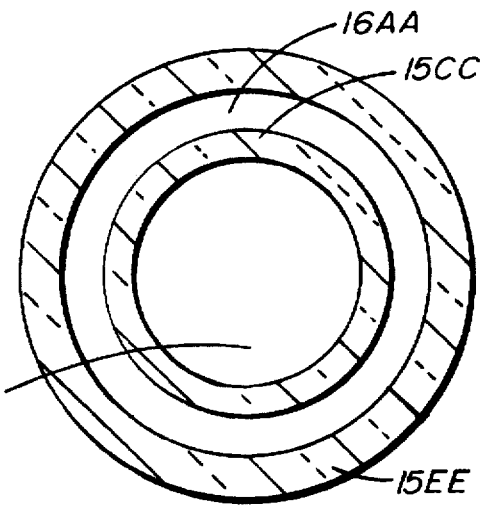
FIG._5F
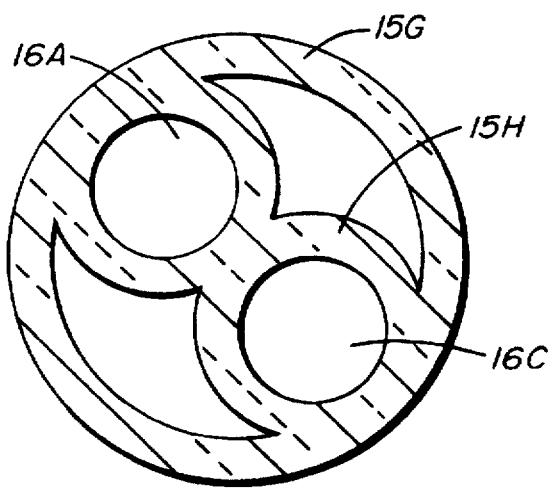
FIG._5G
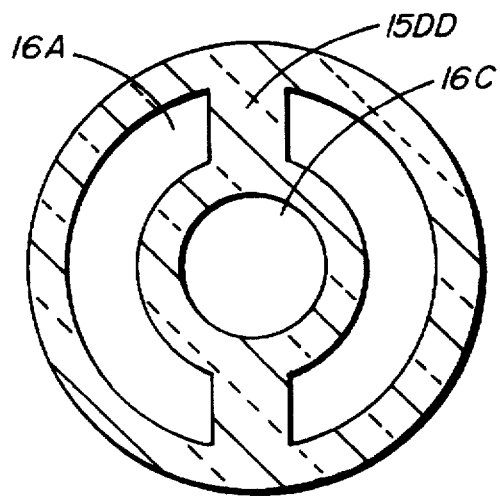
FIG._5H

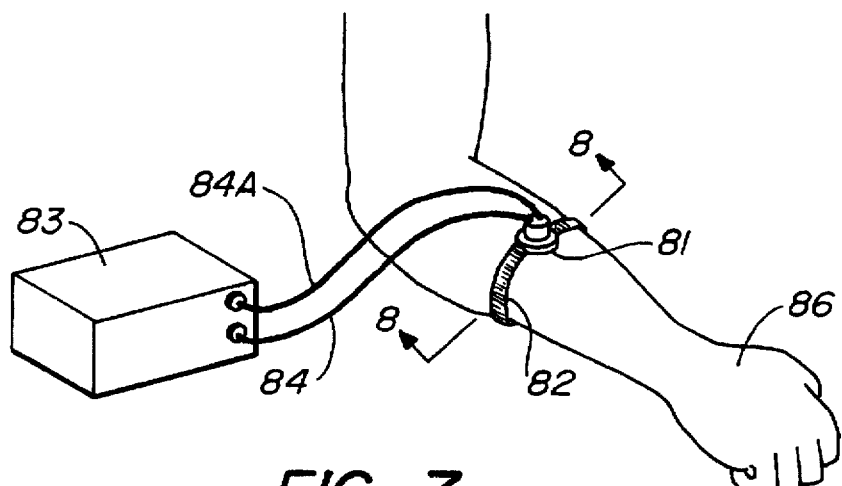
FIG._7
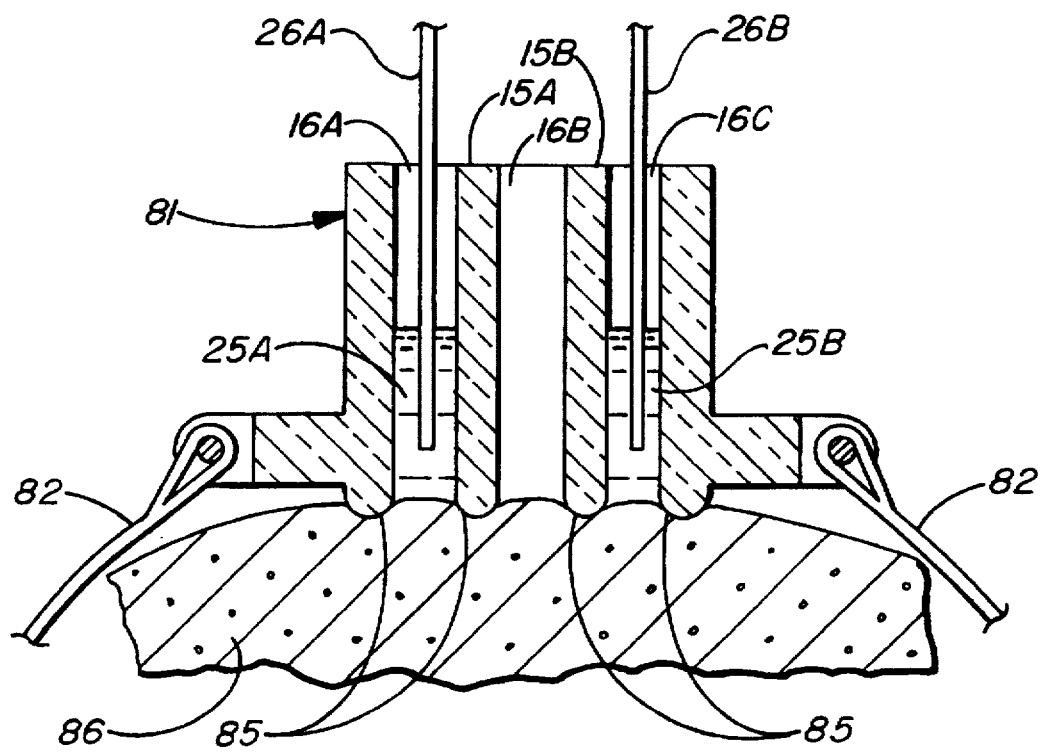
FIG._8

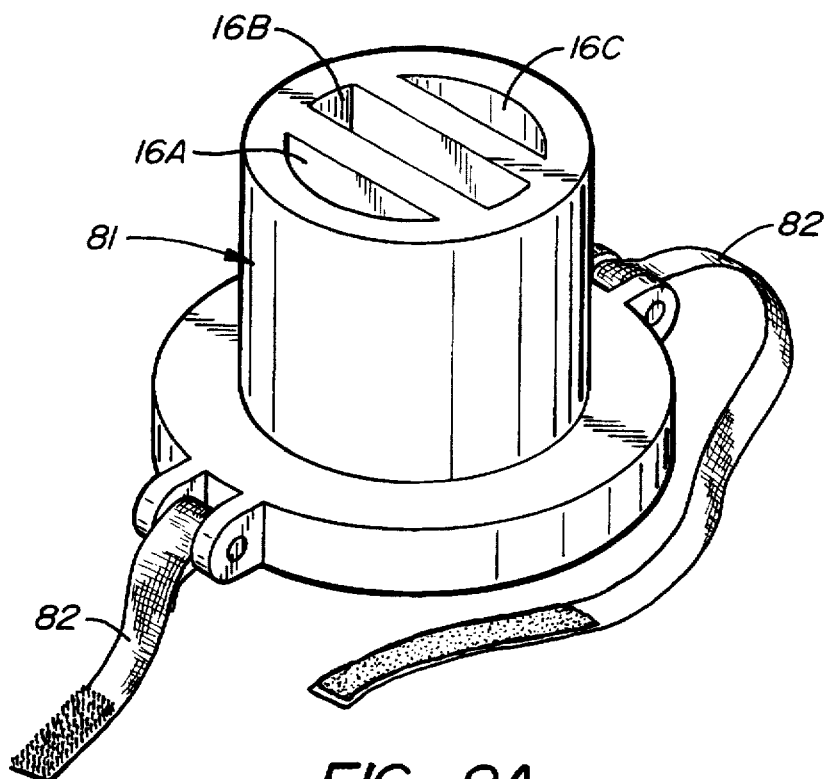
FIG._9A
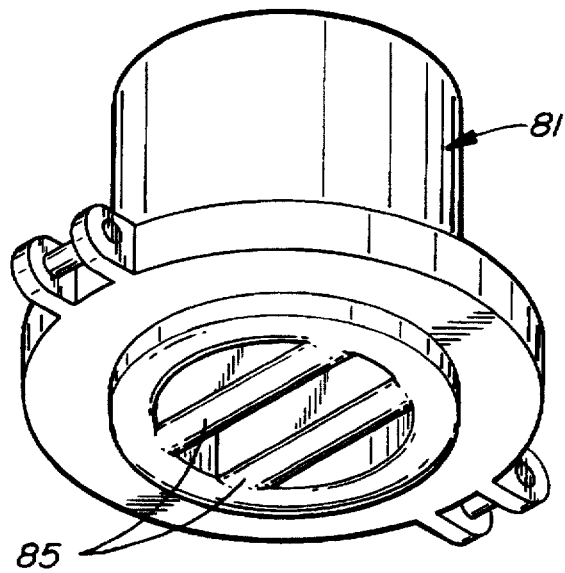
FIG._9B

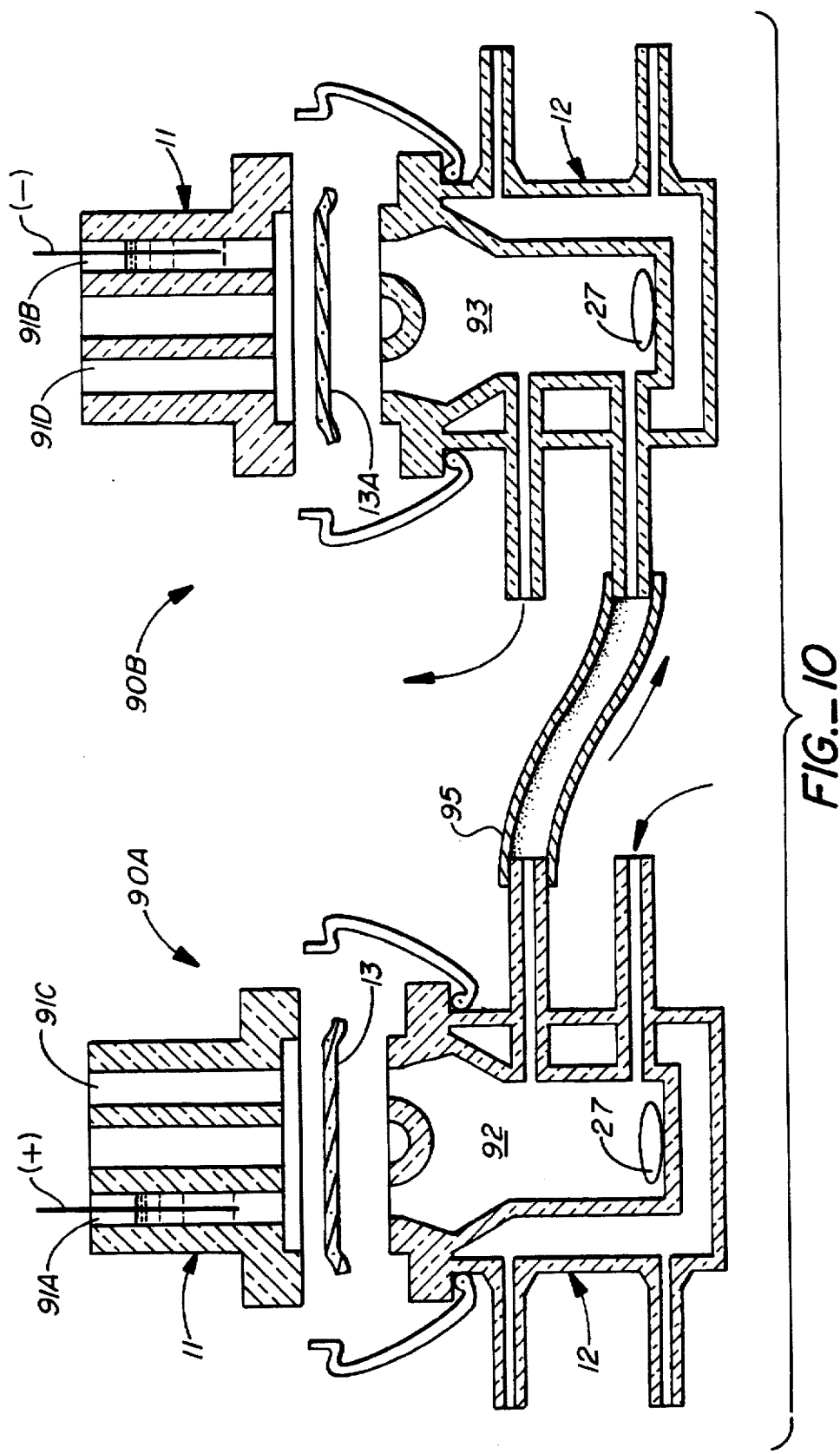
FIG._10

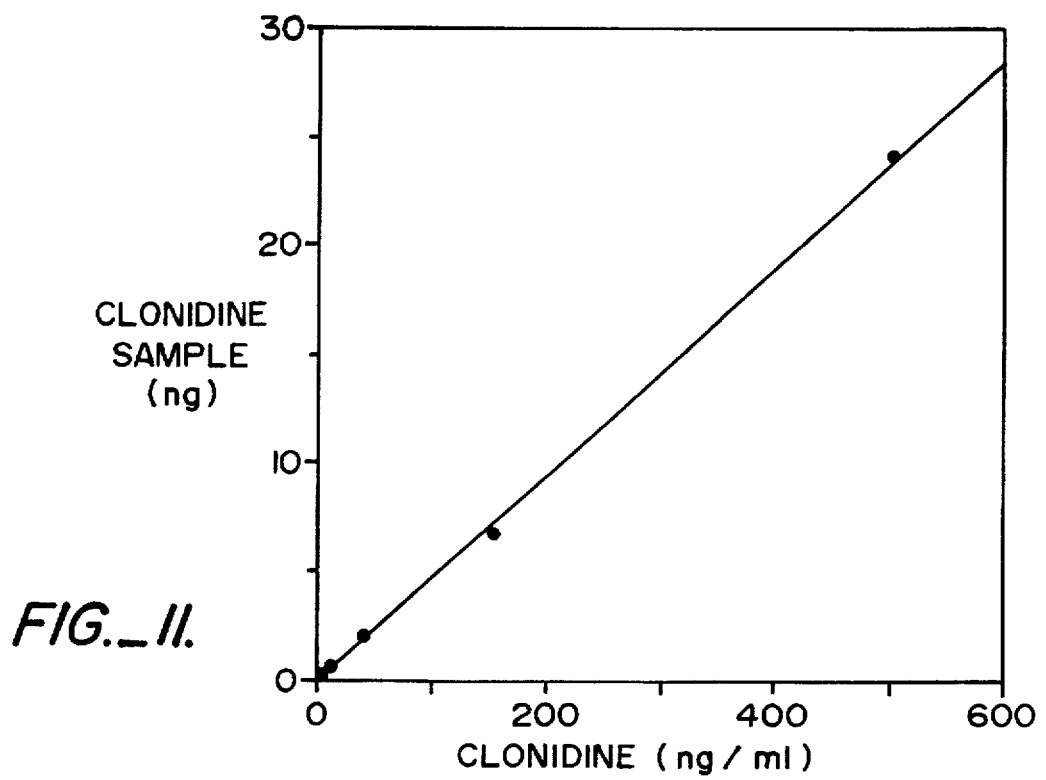
FIG._11.
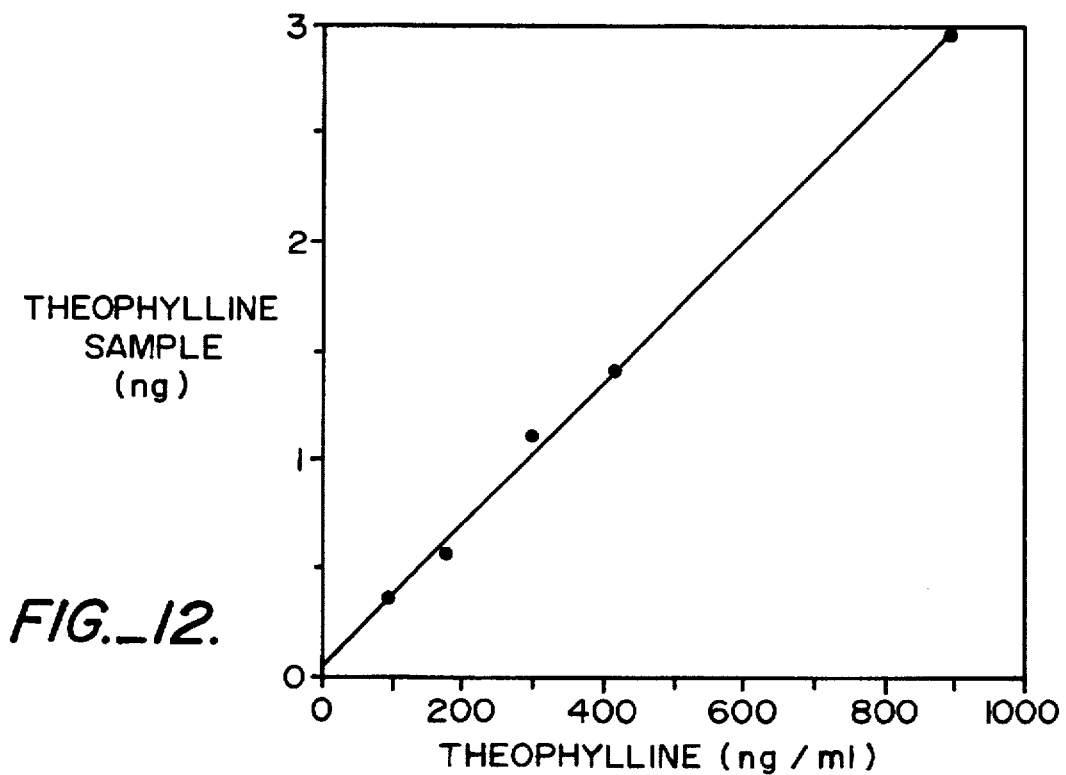
FIG._12.

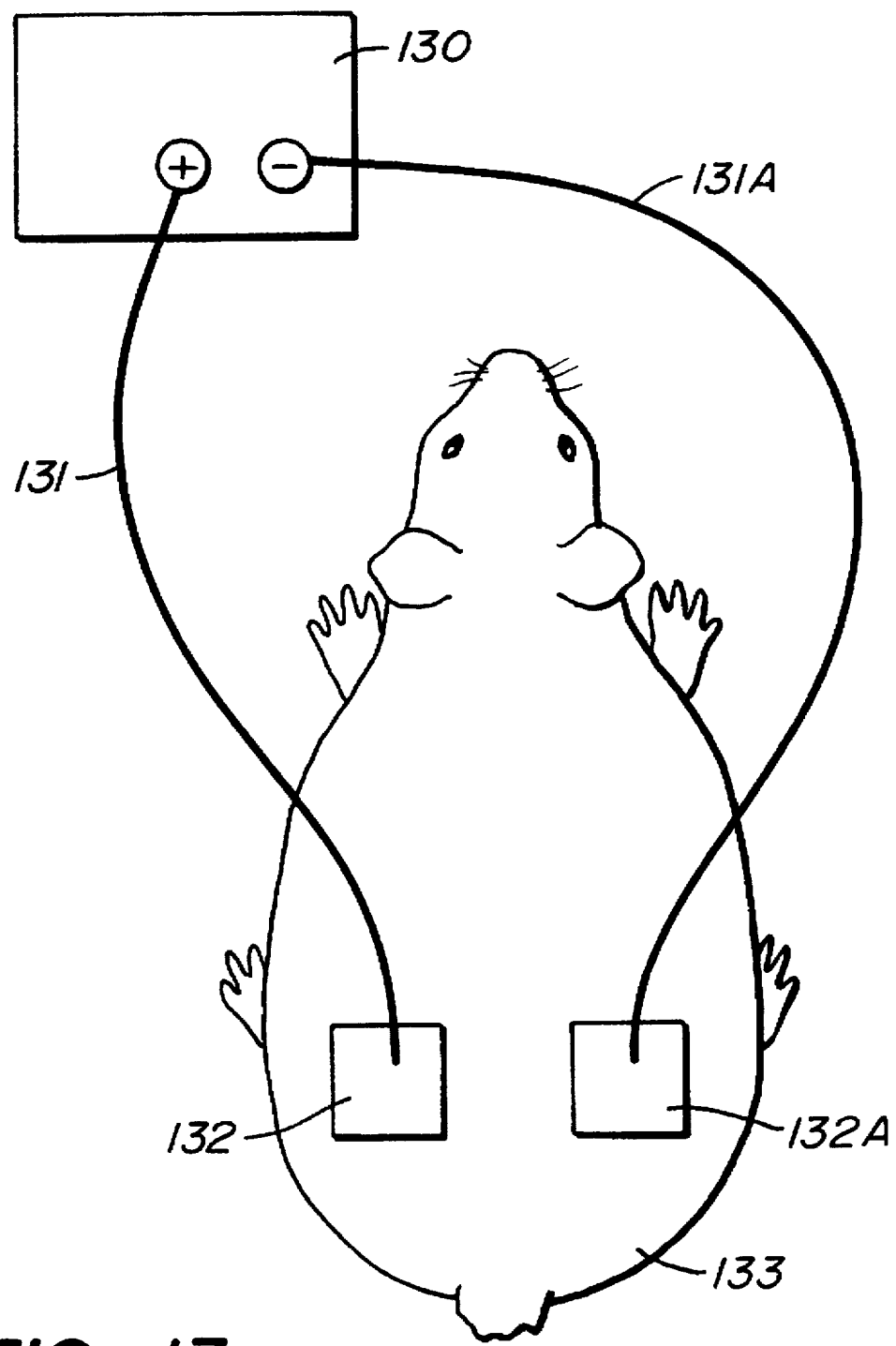
FIG._13.

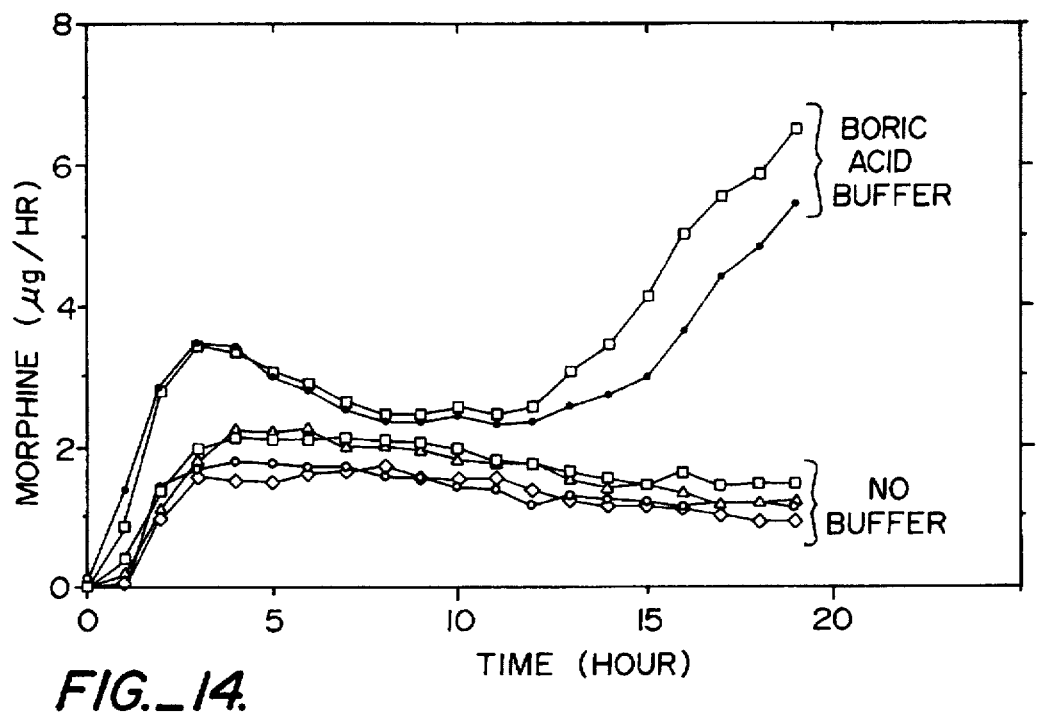
FIG._14.
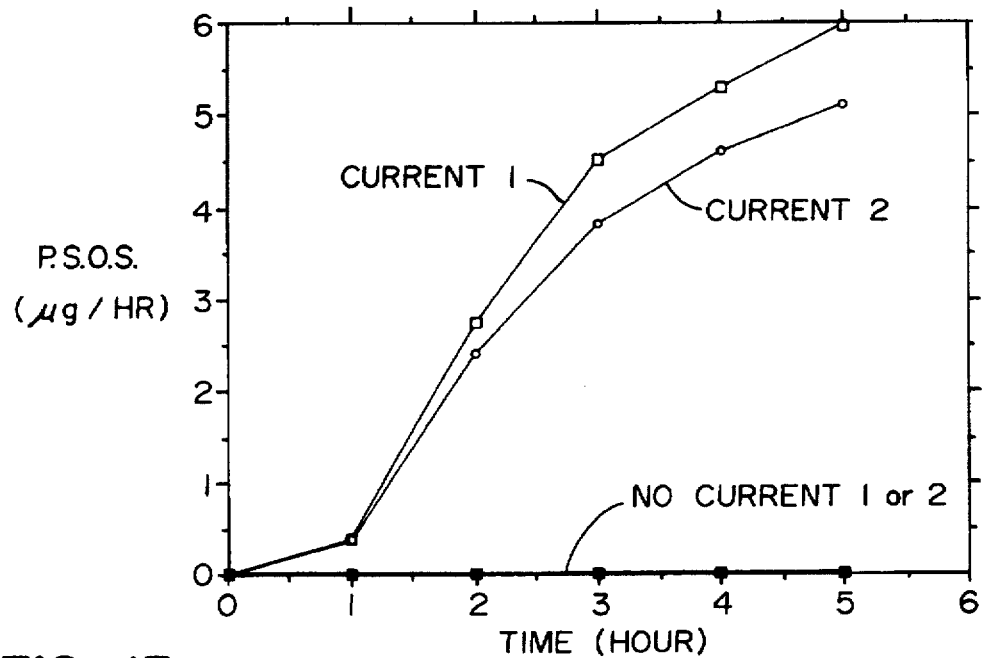
FIG._15.

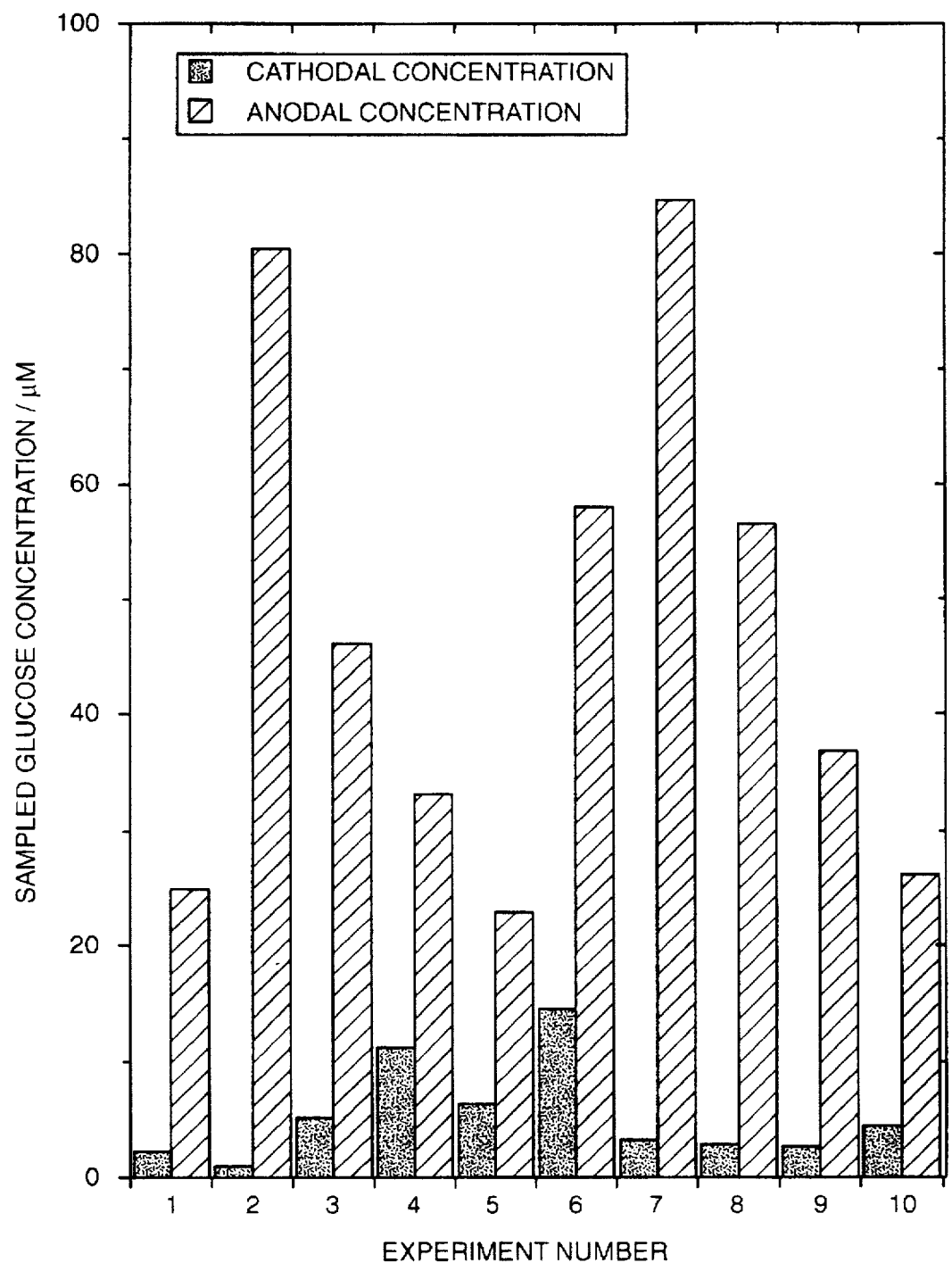
FIG._16

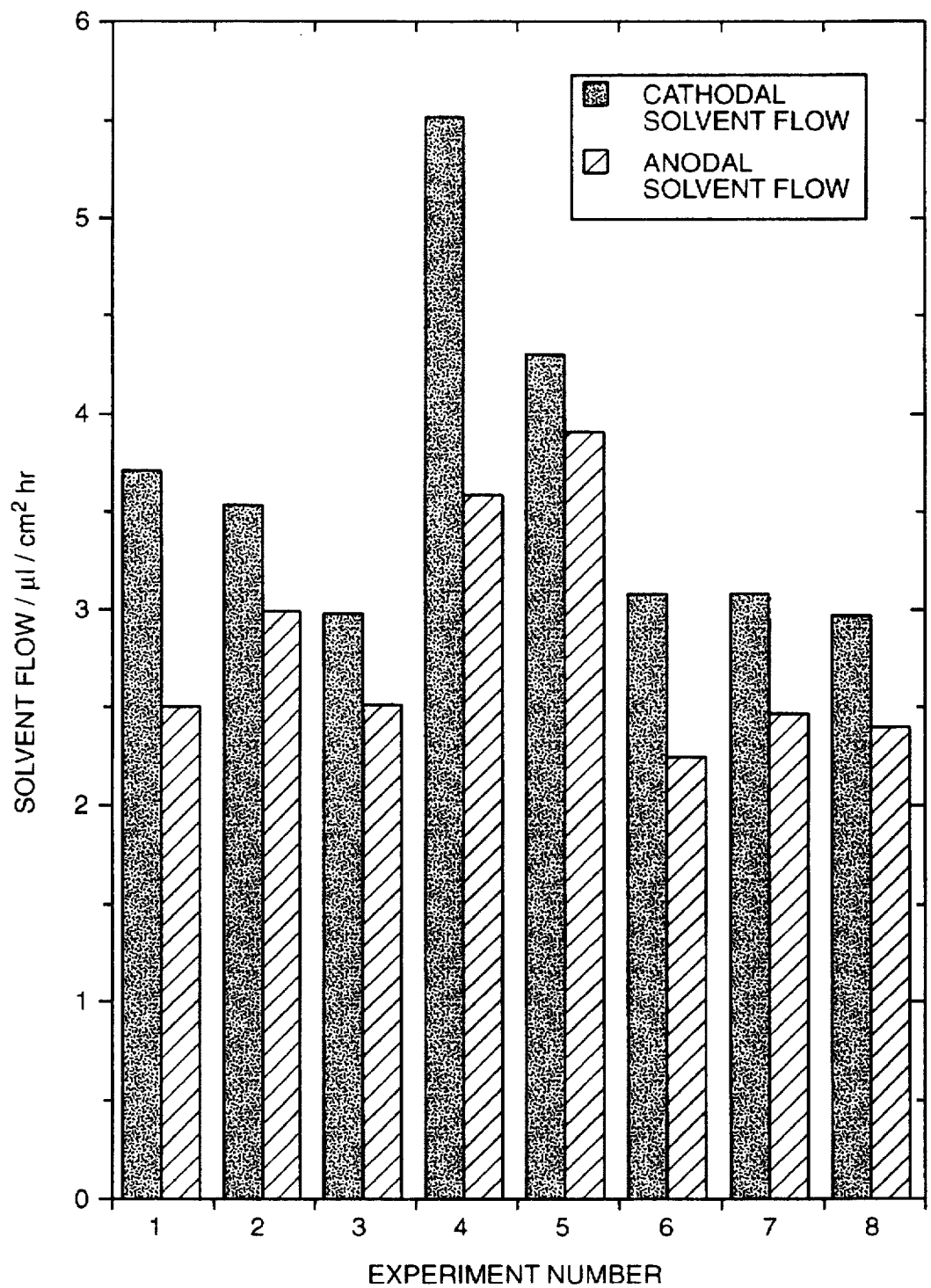
FIG._17

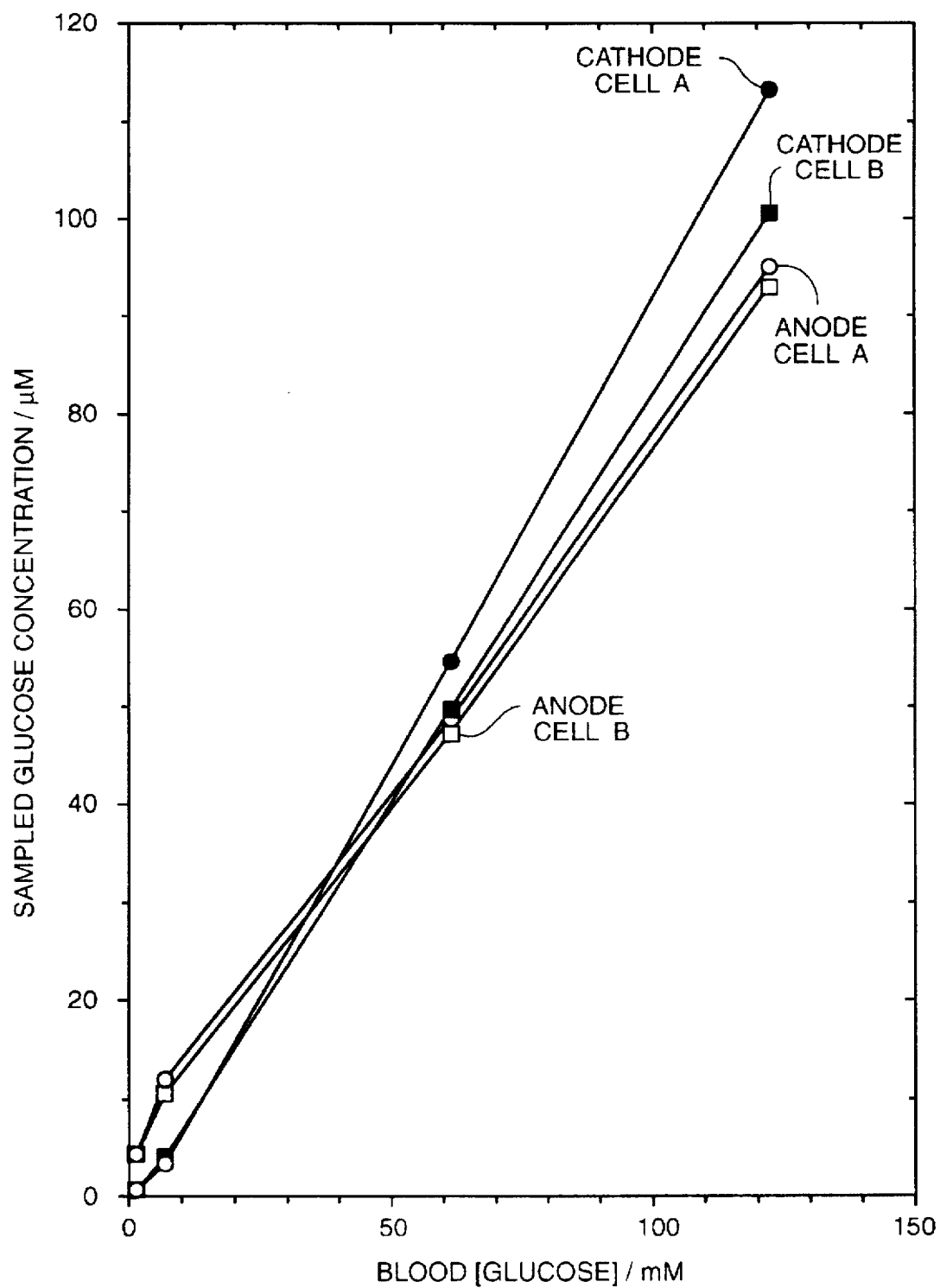
FIG._18

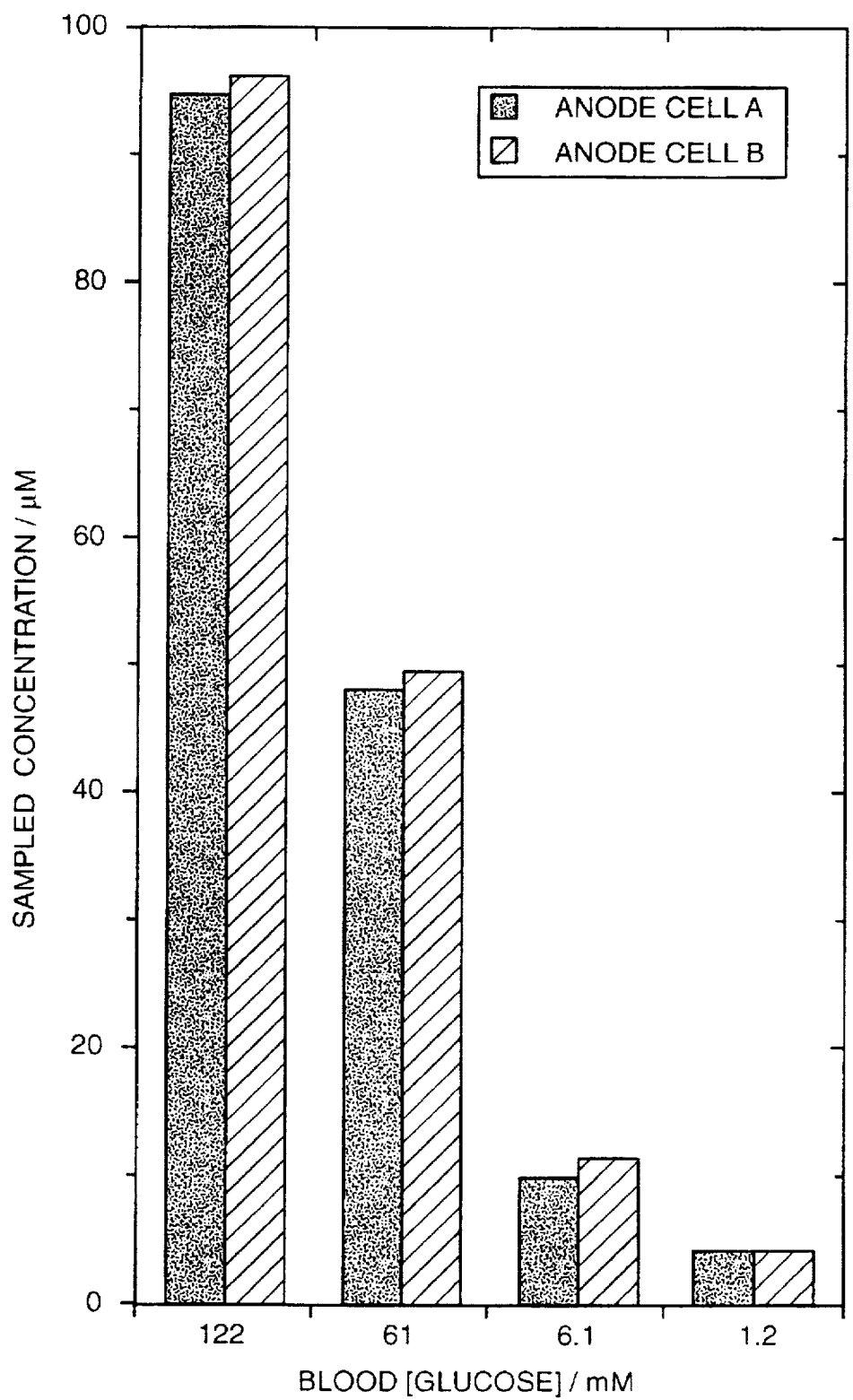
FIG._18A

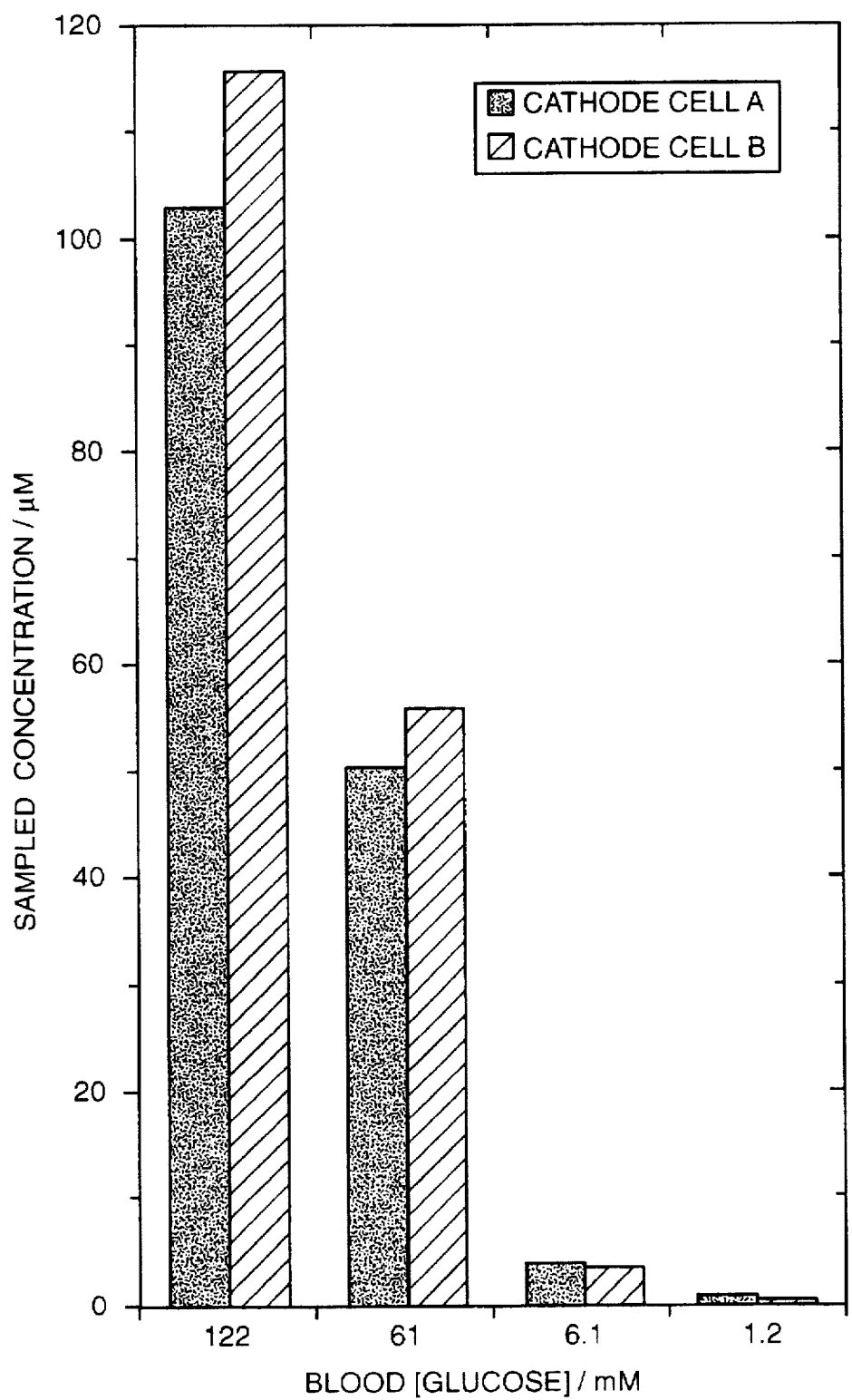
FIG._18B

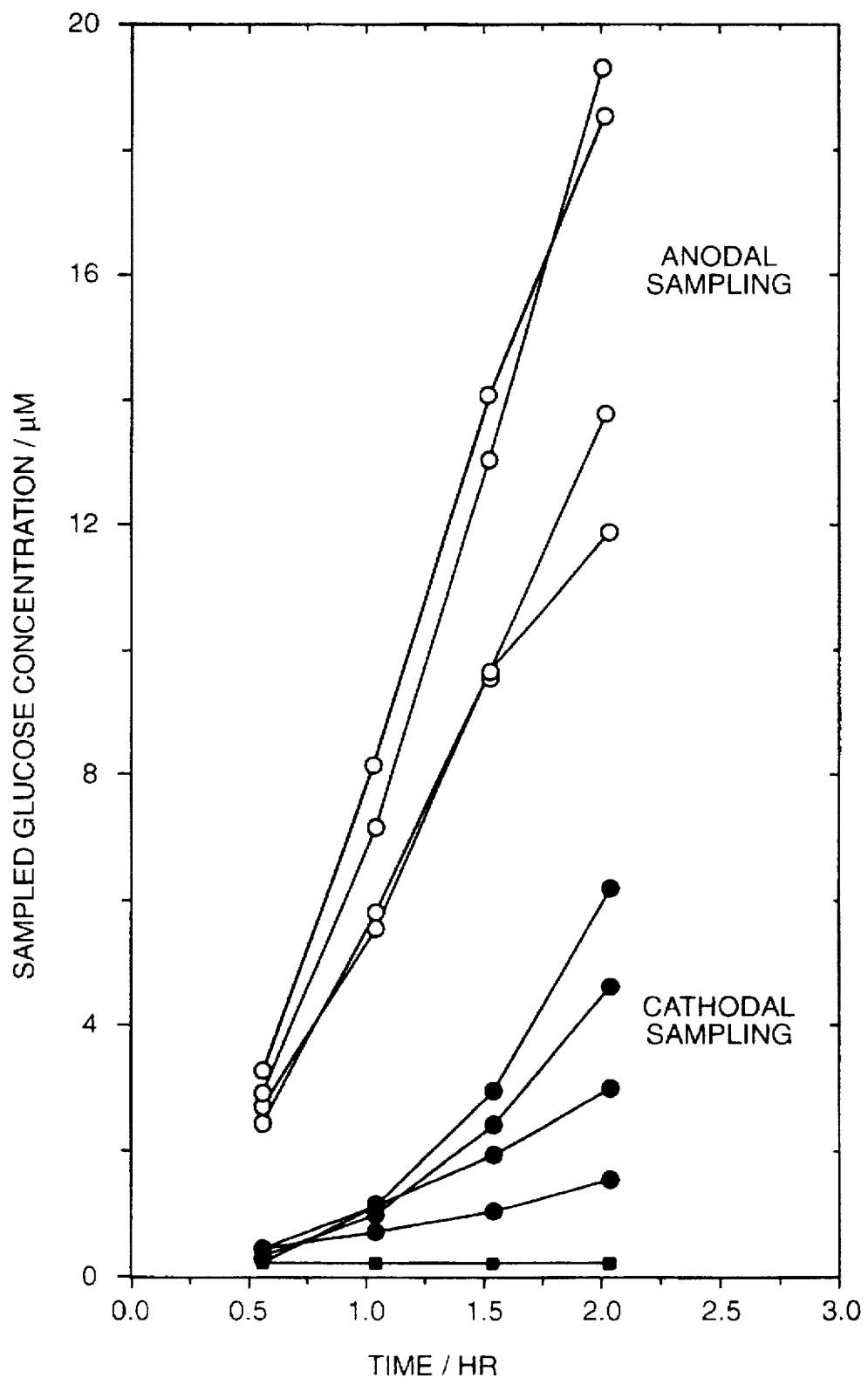
FIG._19

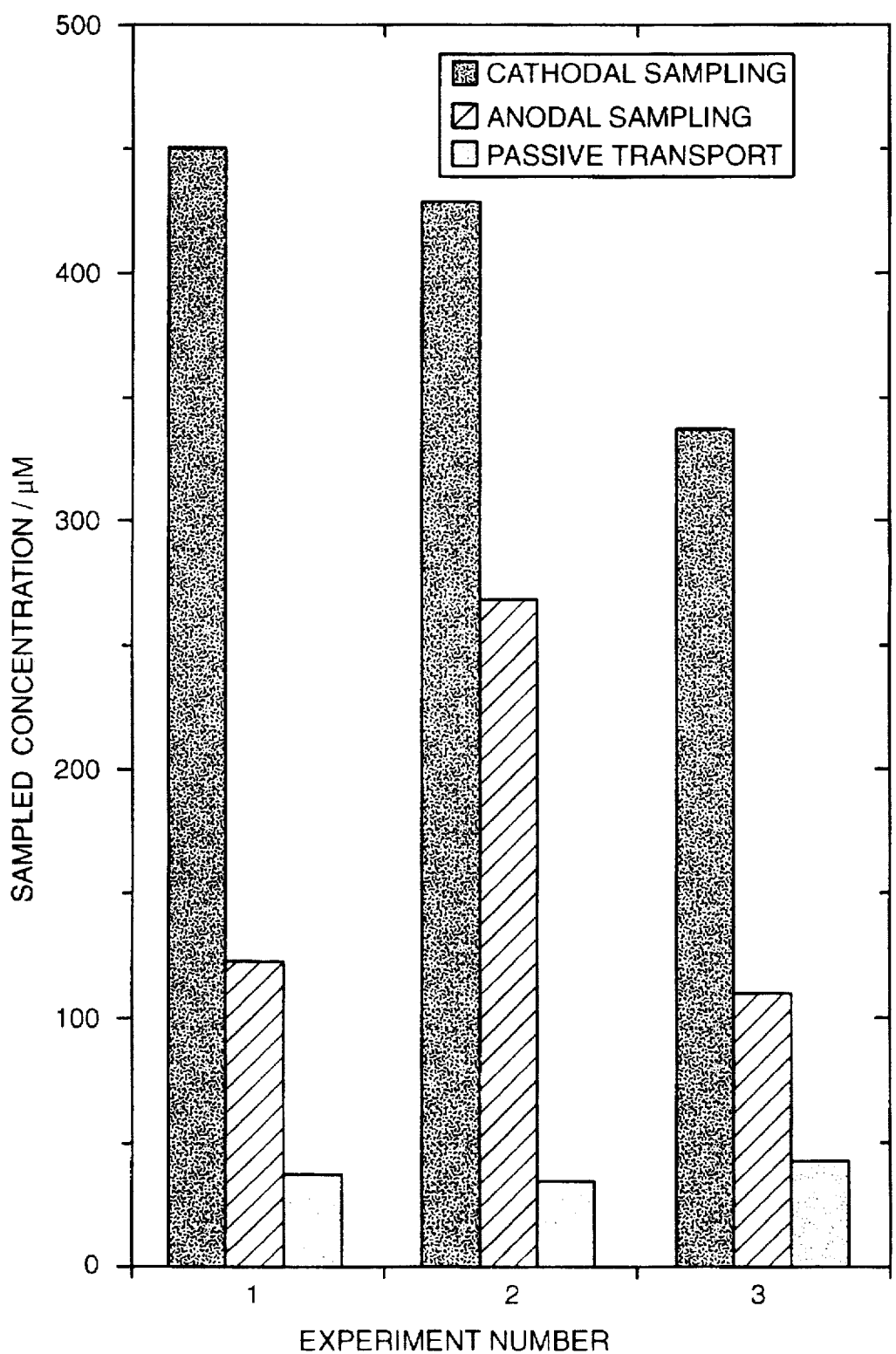
FIG._20

METHOD FOR THE IONTOPHORETIC NON-INVASIVE DETERMINATION OF THE IN VIVO CONCENTRATION LEVEL OF GLUCOSE

This is a continuation of application Ser. No. 771,483, filed on Oct. 4, 1991, now U.S. Pat. No. 5,362,307 which is a continuation in part of U.S. Ser. No. 299,397, filed Jan. 24, 1989, now abandoned, which is a continuation in part application of U.S. Ser. No. 150,159, filed Jan. 29, 1988, now abandoned.

BACKGROUND OF INVENTION

1. Field of the Invention

The present invention relates to a device and to an in vitro method for modeling the iontophoretic sampling or delivery of substances through a membrane, such as the excised skin of a mammal. In another aspect, the present invention relates to a device and to a method for the iontophoretic delivery or sampling of substances through the intact skin of a living mammal. Specifically, the apparatus is a device which placed on the same side of intact skin has a positive electrode, a negative electrode and an electrically insulating material separating the electrodes. In still another aspect the present invention relates to an iontophoretic method of continuously monitoring the levels of bioactive materials in a subject and using a feedback mechanism to maintain effective levels.

2. Description of Related Art

Sampling-In-Vitro

C. C. Peck et al. in *Pharmacology Skin*, Vol. 1, pp. 201–208 published by Karger, Basel 1987, discloses a method to determine in vitro the outward transdermal migration of theophylline using a passive transdermal collection system (TCS). The use of electrical enhancement of the migration is not disclosed.

R. R. Burnette et al. in the *Journal of Pharmaceutical Sciences*, Vol. 75, No. 8, pp. 738–743, published in August 1986 using the standard diffusion cell discloses a comparison of the iontophoretic and passive in vitro transport of thyrotropin releasing hormone (TRH) across excised nude mouse skin. The results indicate that both charged and uncharged TRH fluxes across the excised tissue were greater than those obtained by passive diffusion alone.

In the standard (state of the art) arrangement for in vitro iontophoretic studies (See FIG. 6), the two halves of a diffusion cell are placed horizontally side by side so that the skin is located vertically between them, with its epidermal side facing one half and its inner side facing the other. The bioactive preparation and the active electrode are put in the "epidermal" half of the cell, and the other side of the cell contains the passive electrode in a conductive fluid.

This side-by-side arrangement has several drawbacks and limitations. Since the passive electrode is, in effect, placed "inside" the skin, this configuration is not a good model of the in vivo case. The factors that influence such a non-physiological situation may not be those that are important in the clinical case. In addition, there are questions that cannot be investigated with a side-by-side configuration, such as the possibility of horizontal transport (i.e. within skin layers rather than vertically through the skin) and whether an iontophoretically driven drug is "pulled" back out of the skin by the passive electrode.

A state of the art iontophoretic drug delivery system, the Phoresor, is sold by Motion Control, Inc., 1290 West 2320 South, Suite A, Salt Lake City, Utah 84119.

Delivery-In-Vitro

In modeling studies, iontophoresis is useful to examine chemical transport of charged materials through a membrane, such as an excised skin sample. For instance, N. H. Bellantone, et al. in the *International Journal of Pharmaceutics*, Vol. 30, pp. 63–72, published in 1986, disclose a standard state-of-the-art side-by-side diffusion cell design and electrode configuration for various systems utilized for iontophoresis of benzoic acid (as a model compound) (see FIG. 6). A number of limitations exist with the side-by-side cell design as is discussed further herein.

Delivery-In-Vivo

Iontophoresis is the electrically enhanced transport of charged substances usually bioactive materials. The procedure is a known means of transdermal drug delivery. For instance, in U.S. Pat. No. 4,141,359, by S. C. Jacobsen et al., which is incorporated herein by reference, disclose an improved iontophoresis device for the topical administration of ionic drugs or chemicals through epidermal tissue without mechanical penetration. The positive and negative electrodes are attached to the skin at separate locations. The ionic form of the drug is added to the appropriate electrode and is conducted into and through the epidermal tissue by means of direct current from a power source. A number of problems exist in this type of delivery, where the electrodes are separate.

Sampling-In-Vivo

There is a well-recognized and important need to sample and quantify bioactive substances in the body (typically, the blood). For example, it may be crucial to monitor the presence of a key endogenous biochemical for the purpose a disease diagnosis, or it may be essential to follow, and hence, optimize, the blood level of an administered drug during a chemotherapeutic regimen. Usually, the desired determination is achieved by analysis of a blood sample which is withdrawn invasively via an injected needle into a collection tube.

The passive transdermal collection of theobromine in vivo is also disclosed by C. C. Peck, et al. 1987, supra. No electrical current enhancement of the migration is disclosed.

No literature was found which describes a substantially noninvasive procedure for biomaterial sampling of the systemic circulation. It will require a unique application of iontophoresis to "extract" systemically circulating molecules into a collection device positioned on the skin or mucosal membrane surface. The present invention does not involve puncture of the skin nor of any blood vessel.

Biosensing-In-Vivo

There exists a need to continuously or non-continuously monitor certain key biochemical parameters in hospitalized patients, and a need for a new class of medical devices to obtain real-time, on-line quantitation. A biosensor is a microelectronic device that utilizes a bioactive molecule as the sensing signal-transducing element.

K. W. Hunter, Jr., in *Archives of Pathological Laboratory Medicine*, Vol. III, pp. 633–636, published in July 1987, discloses in a general manner the range of devices and the physical properties which are examined. Hunter also includes a general diagram for a transdermal dosimeter. This reference does not provide needed additional specific information to create an operating biosensing-feedback-drug delivery system.

C. C. Peck et al. in the *Journal of Pharmacokinetics and Biopharmaceutics*, vol. 9, No. 1, pp. 41–58, published in 1981, discusses the use of continuous transepidermal drug collection (CTDC) in assessing drug in-take and pharmacokinetics. It was concluded that when back transfer is minimized, CTDC may be a useful tool to access the amount of drug exposure, etc., but offers little advantage over discrete sampling of other body fluids in the study of other aspects of drug disposition kinetics.

U.S. Pat. Nos. of interest include: 4,329,999; 4,585,652; 4,708,716; 4,689,039; 4,702,732; 4,693,711; 4,717,378; 4,756,314; 4,699,146; 4,700,710; 4,706,680; 4,713,050; 4,721,111; 4,602,909; 4,595,011; 4,722,354; 4,722,726; 4,727,881; 4,731,049; 4,744,787; 4,747,819; 4,767,401.

Y. B. Bannon, European Patent Application Publication No. 252,732 (Jan. 13, 1988) to a transdermal drug delivery system is of general interest.

References of interest include:

W. Scharamm, et al., "The Commericalization of Biosensors," MD&GI, pp. 52–57, published in November, 1987.

A. F. Turner, et al., "Diabetes Mellitus: Biosensors for Research and Management," Biosensors, Vol. 1, pp. 85–115, published by Elsevier Applied Science Publishers, Ltd., England, 1985.

Y. Ikarlyaman, et al., Proc. Electrochem. Soc., 1987, 87–9 (Proc. Symp. Chem. Sens.) 378. CA 107-(22); 207350n.

P. H. S. Tso, et al. Anal Chem., 1987, 59 (19), 2339, CA 107(14); 1262448.

H. Wollenberger, et al., K. Anal. Lett., 1987, 20(5), 857, CA 107(9); 73551.

P. J. Conway, et al., D. A. Sens. Actuators, 1987, 11(4), 305, CA 107(5); 36151.

M. Mascini, et al., Clin. Chem., (Winston-Salem, N.C.) 1987, 33(4), 591 CA 107(5); 35851h.

I. Hanning, et al., Anal. Lett., 1988 19(3–4) 461, CA 105(6); 48993q.

M. Shirchirl, et al., Diabetes Care, 1986, 9(3), 298. CA 105(5): 38426t.

S. J. Churchouse, et al., Anal. Proc., (London) 1986, 2395), 146 CA 105(3) 21117v.

D. A. Gough, et al., Anal. Chem., 1985, 67(12), 2351. CA 103(15); 11925a.

C. Loo, et al., Chem. Eng. Sci., 1985, 40(5), 873 CA 103(5); 34337a.

All of the references and patents cited herein are incorporated by reference in their entirety.

It is desirable to have a device and a methodology to sample (or deliver) substances (charged or neutral) from (or to) a membrane (in vitro) or to sample (or deliver) substances (charged or neutral) from (or to) the intact skin (muscosa, etc.) of a living mammal. The present invention accomplishes these objectives.

SUMMARY OF THE INVENTION

In one aspect, the present invention relates to a method AAA for non-invasively determining the level of an inorganic or organic substance contained in the skin surface, underlying tissue or in the circulating blood of a living human being, comprising (a) placing a collection reservoir of an electrically conducting medium in contact with the skin surface of the human being, wherein said collection reservoir is in electrical communication with the skin surface and a first electrode, (b) placing a second collection reservoir and second electrode in communication with a separate area of the skin surface creating an electric circuit, (c) creating between the first and second electrodes electrical current of ions of sufficient magnitude and duration to cause detectable levels of inorganic or organic substance and/or at least one of its metabolites to migrate from the skin surface, underlying tissue, or the circulating blood into the collection reservoir and electrode and the second collection reservoir and electrode, and (d) analyzing the level of the collected extracted inorganic or organic substance or at least one of its metabolites in the collection reservoir or second collection reservoir.

In another aspect, method AAA further includes:

(e) correlating the level of the inorganic or organic substance or at least one of its metabolites in the skin surface, underlying tissue or blood circulation with the extracted levels of the inorganic or organic substance, at least one of its metabolites or combinations thereof, particularly wherein in step (e) the concentration level of the inorganic or organic substance in the skin surface, underlying tissue or in the circulating blood is correlated by comparison to a predetermined standard using extracted concentration of the inorganic or organic substance or at least one metabolite thereof in the collection reservoir, the second collection reservoir or the sum or the difference of the concentration levels of organic or inorganic substances or their metabolites or products or ratios thereof.

The present invention relates to a diffusion cell device for use in the electrically enhanced sampling of a substance from a membrane surface or the delivery of a substance into or through a membrane surface without mechanical penetration comprising at least two electrically conducting permeable electrode means for contacting the membrane surface, and means for electrically isolating each electrically conducting electrode means from each other, wherein said electrode means are disposed in substantially a side-by-side relationship having sides extending and terminating in a substantially common face surface which contacts immediately adjacent portions of the same side of said membrane surface.

In another aspect, the present invention relates to an in vitro device for the removal or delivery of either ionized or unionized substances from a membrane sample without mechanical penetration, which device comprises:

(a) a positive electrode;

(b) a negative electrode, and (c) electrical insulation between subpart (a) and (b), wherein the positive electrode, and the negative electrode, and electrical insulation are positioned on the same side of the membrane sample.

In another aspect, the present invention relates to a device for the removal of or delivery of ionized substances to a mammal through intact skin or mucosal membrane without mechanical penetration, which device comprises:

(a) a positive electrode, (b) a negative electrode, and (c) an electrically insulating material between subpart (a) and (b), wherein the positive electrode, negative electrode and insulating material are physically positioned so that each present a single common surface of the device for contact with the same side of the skin or mucosal membrane of the mammal.

In another aspect, the present invention relates to the use of iontophoresis to determine the level of a uncharged or charged molecule in a living mammal, and with the use of a feedback mechanism, administer appropriate levels of therapeutic substance by any number of available administration routes.

In another aspect the invention relates to the use of iontophoresis to enhance the collection Of a charged or neutral substance from a membrane or the skin of a living mammal at one electrode followed by analysis of the concentration of the substance by gas chromatography (GC), mass spectrometry (MS), by high pressure liquid chromatography (HPLC), scintillation counting, and the like.

BRIEF DESCRIPTION OF THE DRAWINGS

FIG. 1 shows an isometric view of the in vitro diffusion cell configuration for the modeling of the iontophoretic removal or delivery of a charged or neutral substance.

FIG. 2 shows the cross sectional view of the modeling diffusion cell of FIG. 1 along line 2—2.

FIG. 3 shows an exploded cross-sectional view of the diffusion cell of FIG. 2.

FIG. 4 shows an exploded cross-sectional view of the cell of FIG. 2 wherein solid glass is the insulator in the lower reservoir separating the electrodes. FIG. 4 also shows the circulating system for the receptor liquid.

FIGS. 5A to 5H shows a cross-sectional view of a number of configurations for the positive electrode, negative electrode and insulating means therebetween taken along line 5A—5A of FIG. 1 for the bottom of the upper portion of the diffusion cell.

FIG. 6 shows an isometric view of the state of the art side-by-side iontophoresis cell.

FIG. 7 shows an isometric view of an iontophoresis cell as it is used for in vivo delivery of a bioactive molecule to a human patient.

FIG. 8 shows a cross-sectional view of the diffusion cell of FIG. 7 along line 8—8.

FIGS. 9A and 9B shows a top and a bottom view of an iontophoresis diffusion cell of FIGS. 7 or 8.

FIG. 10 shows a cross-sectional view of an iontophoresis experiment wherein the electrodes are separated.

FIG. 11 shows the iontophoretic in vitro sampling of clonidine using the diffusion cell of FIGS. 1, 2 or 3.

FIG. 12 shows the iontophoretic in vitro sampling of theophylline using the diffusion cell of FIGS. 1, 2 or 3.

FIG. 13 shows the separated electrodes connected to a guinea pig in either a delivery mode or a sampling mode for a charged or uncharged substance.

FIG. 14 shows the iontophoretic in vitro delivery of morphine using the diffusion cell of FIGS. 1, 2 or 3.

FIG. 15 shows the iontophoretic in vitro delivery of P.S.O.S. (potassium sucrose octasulfate) using the diffusion cell of FIGS. 1, 2 or 3.

FIG. 16 is a bar graph representation the iontophoretic device results obtained from ten different mice for glucose.

FIG. 17 is a bar graph summary of iontophoretic experiments to show the skin is permselective for sodium ions in the solvent flow during iontophoresis.

FIG. 18 is a graphic representation of the iontophoretic experimental results showing how reproducible iontophoretic sampling is on the same piece of skin.

FIGS. 18A and 18B are bar graph representations showing the sampling is linear as a function of dermal side glucose concentration.

FIG. 19 is a line graph representation of glucose sampling kinetics.

FIG. 20 is a bar graph representation of iontophoretic device sampling results for sampling of ethanol.

DETAILED DESCRIPTION OF THE INVENTION AND PREFERRED EMBODIMENTS

Definitions

As used herein:

"Diffusion cell" refers to the electrical system for iontrophoresis. The system may include positive electrode, negative electrode and electrical insulation therebetween. The system may also be a positive lead, electrical insulation and ground.

"Mammal" refers to the usual laboratory animals used in experimentation rats, mice, guinea pigs, rabbits, monkeys and the like. The term may also include dogs, cats, cattle, sheep, horses and the like. A preferred mammal is a human being.

"Membrane surface" refers to either a thin membrane such as excised skin, synthetic membranes, mucosal membranes or to the surface and below the intact skin of a mammal, preferably a human being.

A preferred embodiment for sampling or delivery is the combination of materials for the permeable electrodes.

A more preferred embodiment of the electrodes includes a metal wire in combination with a gel which is in contact with the membrane surface.

General Materials and Methods for Sampling or Delivery

Biomaterial or biomaterials delivered or sampled 5 includes anything found in the system of a living mammal such as degradation products, metal ions, peptides, hormone toxins, and the like—neutral species or those which carry or can be made to carry an electrical charge.

In the sampling and in the delivery electrode (which are open), the electrically conducting gel is KENZGELELC available from NITTO Electric Industrial Co., Osaka, Japan.

Voltage is normally between about 0.1 and 15 volts, preferably between about 1 and 10 volts, and especially about 5 volts for both sampling and delivery.

In-Vitro-Sampling

Description of modeling cell: Refer to FIGS. 1, 2, 3 and 4. The iontophoretic diffusion cell 10 for in vitro model sampling is constructed so that one half of the cell 11 is above the other half 12. The excised skin 13 is interposed horizontally with the epidermal surface 14 interfacing with the upper half of the cell (see FIGS. 1, 2 or 3). The upper half of the cell 11 is divided by two vertical walls 15A and 15B into three chambers 16A, 16B and 16C. The outer two chambers are therefore separated by an intervening space 16B (the third chamber). The lower half of the cell 12 holds the receptor fluid. The walls 15A and 15B that form the middle chamber 16B in the upper half 11 are continued as walls 15C and 15D into the lower half of the cell 12, but are then joined to form a trough 18 producing a channel 19 which traverses the top of the lower half of the cell 12. Channel 19 may have sampling ports to remove liquid.

Chambers 16A and 16C each independently contain an electrically conducting means or medium 25A (or 25B) selected from a gel, liquid, paste, sponge, foam, emulsion, permeable metal, permeable ceramic or combinations thereof. To complete the electrical circuit, usually metal wires or electrodes 26A and 26B are each placed in the electrically conducting medium as shown in FIG. 3. The other similar FIGS., e.g. 1, 2, 3 or 4 can be interpreted in the same manner.

When the upper half of the cell 11 is positioned over the lower half 12 so that the upper walls 15A and 15B and lower walls 15C and 15D coincide, the strip of skin 13 between the walls is sealed off from the skin in the electrode chambers on both its upper and lower sides (FIG. 2). The portions of skin in the electrode chambers 16A and 16C are thus physically and electrically isolated from each other so that the flow of current and biomaterial through and within the skin can be investigated. Ports 20A and 20B in the lower half cell 12 allow receptor fluid 17 to be continuously perfused. Ports 21A and 21B allow for constant temperature liquid monitoring of water jacket 21C. During an experiment, the channel 19 at the top of the lower half of the cell 12 is filled with receptor fluid 17 so that the underside of the skin 13 remains moist. The walls 15C and 15D of the channel also provide mechanical support for the membrane (skin).

The upper half 11 and lower half 12 are combined at their complementary single plane faces, having the sample 13 therebetween, using spring clips 22A and 22B or other fastening means to keep the upper half 11 and lower half 12 of the cell tightly joined together.

In FIG. 4, barrier 18A is made of glass to electrically insulate chambers 16A and 16C. FIG. 4 also shows the receptor liquid 17 moving in line 20B to a container 29A. The liquid 29B is then pumped using a pump 29 back to the reservoir (or vice versa). Any suitable liquid, saline, blood and the like may be used in both substance sampling or delivery experiments for substances.

Shown in FIGS. 5A to 5H are several embodiments of the spatial configuration of the diffusion cell 10 of the present invention along line 5A—5A of FIG. 1. FIG. 5A is a cross-sectional view of the bottom of the upper half of FIG. 1 taken across line 5A—5A. Chambers 16A, 16B and 16C and electrical isolating materials 15A and 15B (e.g. glass walls) are shown. In FIG. 5B is a cross-sectional view along line 5—5 having chamber 16A and 16C and a single glass wall 15E. Cross-sectional view 5C has square chamber 16A, 16B and 16C with electrically insulating walls 15A and 15B. The cross-sectional view of FIG. 5C has square chambers 16A and 16C and a single glass wall 15F. The cross-sectional view in FIG. 5E shows a concentric coaxial configuration. The chambers 16AA(+), 16BB (insulating) and 16CC(−) are shown having insulating glass walls 15AA and 15BB and 15EE. The cross-sectional view of FIG. 5F also shows a concentric cell having chambers 16AA(+) and 16CC(−) and insulating wall 15CC and 15FF. FIG. 5G is an cross-sectional view of electrodes and insulation having two circular electrodes (chambers 16A and 16C) and glass insulating walls 15G and 15H. FIG. 5H is a cross-section of a type or concentric cells along line 5A—5A having chambers 16A and 16C with insulating wall 15DD. These configurations appear on the bottom of upper half 11 and the top of lower half 12 and the walls and chamber coincide when the cell is closed as shown in FIG. 1.

Of course, the top of upper half 11 is shown having an open top to the chambers 16A to 16C. This top may be closed or covered. In this way, the chambers 16A and 16C containing the electrode wires could be positioned at many angles from the vertical, and the chambers 16A and 16C would retain good electrical contact with the membrane surface.

To maintain a solid electrical contact, a chemical adhesive which is not susceptible to iontophoresis, such as the hypoallergic chemical adhesive available from 3M Company, St. Paul, Minn., may be used.

A non-invasive method and device for sampling and monitoring of non-ionic moieties, such as glucose, sucrose and the like, using iontophoresis is described.

Glucose—Medical diagnosis and patient care rely upon sampling and analysis of bioactive substances in the body. Typically, sampling involves analysis of the blood and plasma which implies an invasive, inconvenient, risky (e.g. viruses) and some times limited blood sampling. One of the most important cases where sampling is needed, at least several times a day for life time, is in the case of patients having sugar diabetes. Real time information concerning the glucose levels in the body (e.g. blood) is most important information in the patient's treatment and in many cases-often a question of life and death. A simple non-invasive sampling method using iontophoretic sampling is now described.

In order to show the ability of the method to sample glucose through the skin, in vitro studies are conducted using hairless mouse skin as the skin model and the iontophoretic diffusion cells in FIGS. 1–13. The results here are applicable to in-vivo sampling from a mammal, particularly a human being. Two self-adhesive gel electrodes (Kenzgelelc, by Nitto Electric Industry Co., Limited, Osaka, Japan) are placed on the same side of a single continuous piece of hairless mouse skin (full thickness-about 0.5 mm) (Skh: hr-1, 8–13 weeks old). Under the skin, radiolabelled ($^{14}$C—U)-glucose having known concentration in solution in phosphate-buffered saline (0.9% sodium chloride) is perfused, pH of phosphate is about 7.4. Temperature is ambient.

In the first set of experiments, following the assembly of the cell and initiation of the glucose solution perfusion, current is applied (0.5 milliampere) for 2 hours. The voltage may vary from about 1 to 10 volts. Usually, it is about 5 volts. The important parameter to keep constant is the applied current. The voltage may vary based upon the electrical resistance of the sampling site. Then the gel electrodes are disconnected and tested for radioactivity content by conventional liquid scintillation counting. When the glucose concentration under the skin is changed from 1.07 mg/ml to 0.153 mg/ml (a factor of 0.143), the amount sampled through the skin in 2 hours is changed from 4.9 µg to 0.705 µg (a factor of 0.144—see Table 1). The results demonstrate that for a fixed sampling time under the same electrical conditions, a near-perfect linear correlation between the glucose concentration in the skin and the amount of glucose sampled, is obtained at the (+) electrode. (Electrical conditions in the experiments—same constant direct current (dc) but as iontophoretic delivery may also operate in pulsed current, etc., (the pulsed approach should also perform in a predictable way for sampling).

In a general sense more than one level or ratio of extracted or organic or inorganic substances or metabolites may be used to correlate concentration levels in vivo.

Glucose—In another aspect of the present invention, glucose is extracted as expected at the cathode chamber. However, significant quantities of glucose metabolites migrate to and are extracted at the anode. This is a completely unanticipated and surprising discovery. Glucose is apparently subject to metabolism during its passage through the skin. The products of this biotransformation are believed to be organic acids, such as pyruvic acid and lactic acid. At physiological pH, these metabolic acids are negatively-charged, and are drawn by electrostatic forces to the positive electrode. This is a stronger attraction than that possible via electro-osmosis. Further, the levels of extracted material found at the anode are greater than that at the cathode. Instead of obtaining only one piece of information related to the subdermal glucose concentration, therefore, at least two measurements are generated:

(1) the glucose extracted to the cathode, and
(2) the metabolites drawn to the anode.

In addition, while 90+% of the material found at the cathode is intact glucose, only about 20% of the extracted species at the anode is glucose. The rest of the material comprises one or more metabolites, e.g. lactic acid, pyruvic acid etc. The absolute quantity of material at the anode, furthermore, is more than double (on a molar basis) that found at the cathode, again reflecting the greater efficiency by which charged substrates are mobilized by their iontophoresis. Thus, sensitivity is improved considerably in a number of ways:

(1) Glucose is present to be detected at both electrodes, in different amounts, providing the possibility of a "difference" or "sum" or "ratio" measurement;

(2) The metabolite levels are high, which makes the assay more straightforward, and/or shortens time of iontophoresis necessary for the "test" to be performed; and (3) The relationship between metabolite levels in the anode compartment and the glucose amounts in the cathode and anode chambers are used productively to better define how the sampling reflects the blood concentration of the sugar.

TABLE 1

GLUCOSE SAMPLE

| Concentration [mg/ml] | Iontophoretic Flux sample (µg/2 hr) |
|---|---|
| A 0.153 | 0.705 +/− 0.095 |
| B 1.07 | 4.9 +/− 0.7 |
|  | (+/− 14%) |
| Ratio A/B 0.143 | 0.144 (Found) |

In the second set of experiments, using similar experimental set-up as before, a ($^{14}$C—U)-glucose solution of 0.34 mg/ml glucose is phosphate buffered saline is perfused, and the gel electrodes are replaced every 30 minutes.

Evaluation of the glucose sampled into the electrode gel shows a repeatable amount of radioactive glucose—0.8 µg/0.5 hr. with a standard deviation (S.D.) of ±23% (see Table 2). Since the skin for each single experiment comes from a different mouse, evaluation of each single diffusion cell (means—samples collected through the same piece of skin), eliminating the first sample (the first 0.5 hr. is slightly higher than the others due to the experimental conditions) was done. The experimental values obtained of 0.79 to 0.74 µg are an average of the amount of glucose found in four separate cells.

TABLE 2

GLUCOSE SAMPLING

| Sample | Time (hr) |  | Sample-glucose (µg) |
|---|---|---|---|
| 1 | 0−½ |  | 0.97 +/− 0.12 |
| 2 | ½−1 |  | 0.79 +/− 0.09 |
| 3 | 1−1½ |  | 0.76 +/− 0.10 |
| 4 | 1½−2 |  | 0.75 +/− 0.21 |
| 5 | 2−2½ |  | 0.74 +/− 0.24 |
|  |  | Average | 0.80 +/− 0.19 |
|  |  |  | (+/− 23%) |

Concentration of glucose is 0.34 mg/ml
Flow rate of glucose solution is 15 ml/hr
n=four cells were averaged for each sample It is demonstrated that the S.D. for individual diffusion cells, means individual mouse, are within the range of 4 to 9% (except for cell #3)—see Table 3.

TABLE 3

GLUCOSE SAMPLING

| Cell* | Amount Glucose Measured In Gel Electrode per Sample (µg) |
|---|---|
| 1 | 0.825 +/− 0.041 |
|  | (+/− 5%) |
| 2 | 0.963 +/− 0.090 |
|  | (+/− 9%) |
| 3 | 0.530 +/− 0.115 |
|  | (+/− 22%) |
| 4 | Cell broken |
| 5 | 0.727 +/− 0.033 |
|  | (+/− 4%) |

Concentration of glucose is 0.34 mg/ml
Flow rate of glucose solution is 15 ml/hr
n=Averages of four cells for each of four time periods It is demonstrated that glucose is iontophoretically sampled accurately by the present invention. There is a clear correlation between the amount of glucose under the skin, and the amount of glucose that is sampled. The glucose amounts sampled are significant and repeatable and therefore reliable. Since it is known that iontophoretic transport is linearly dependent upon current and duration of current flow these parameters are safely manipulated (within safe limits for current concentration) in order to obtain detectable amounts of glucose in the gel electrode. This method is not limited to transdermal sampling and is possible through mucosal surfaces (e.g., nasal, buccal) where the barrier for non-ionized species transport is much lower, and the concentration of blood vessels is high.

The combination of this sampling procedure with specific glucose biosensor (e.g., J. C. Cooper, E. A. H. Hall, *Journal of Biomedical Engineering*, Vol. 10, pp. 210–219, published in 1988), or glucose selective electrodes (R. L. Solsky, *Analytical Chemistry*, Vol. 60, #12, 106R–113R, published in 1988), or in situ analysis (e.g., colorimetric) provides real time glucose information, which references are incorporated herein by reference.

Combination of the above monitoring, which provide real time medical information with delivery device (e.g., insulin pump, iontophoretic insulin delivery device) produces a useful closed-loop, "feed-back" drug delivery system.

Drugs whose levels in a human being are sampled and monitored by the present method include, but are not limited to:

| Agent | For |
|---|---|
| Theophyline treatment | Blood levels for asthama |
| Fluorouracil methotrexate | Blood levels in cancer chemotherapy |
| Metal ions K$^+$, Na$^+$, Cu, Fe$^{+++}$, etc. | Examine blood levels |
| Accidental poisoning | Where invasive blood sampling is to be avoided |
| Concentration of suspect agent | No invasive concentration of agent |
| Hormone levels | Monitor blood levels |
| Prostaglandin (nasal) steroids (anabolic cancer treatment, male or female hormone adjustment) | Monitor blood levels |
| Antidepressants amitriptylene.HCl | Sample and monitor blood levels |

The present invention is useful in determining metabolic glucose levels in a mammal, preferably a human being. Both hypoglycemic and hyperglycemic conditions are monitored, e.g. from a glucose level in milligrams per milliliter of blood of about 0.1 mg/ml to 5.0 mg/ml. A preferred range for monitoring hypoglycemia is between about 0.3 and 0.7 mg./ml. A preferred range for hyperglycemia (diabetes) between about 1.0 and 5.0 mg/ml. A normal blood glucose level is between about 0.8 and 1.1 mg glucose/ml of blood.

Biosensors for detection at concentration levels of interest are commercially available for the analysis of lactate, alcohol, sucrose, glactose, uric acid, alpha amylase, choline and L-lycine, and all are indirect amperometric based on oxygen consumption or hydrogen peroxide production. There are a few commercially available biosensors which are based on alternative methods of detection. The most important of these from a commercial point of view is the NAIAD automatic chemical warfare agent detector.

The ExacTech (Baxter Travenol, Deerfield, Ill.) biosensor for glucose is a second generation biosensor of amperometric operation. Oxygen is replaced by an artificial electron mediator, which shuttles the electrons from the biological component to the electrode. Such revolutionary mediators: (1) exhibit ready participation in redox reactions with both the biological component and the electrode; (2) show stability under the required assay conditions; (3) do not tend to participate in side reactions during transfer of electrons, such as the reduction of oxygen; (4) exhibit appropriate redox potentials away from that of other electrochemically active species that may be present in samples; (5) are unaffected by a wide range of pH; are non-toxic, especially for in vivo applications; and (6) are amenable to immobilization.

The ExacTech glucose test is easily performed and a result is obtained within 30 seconds of applying the whole blood sample to a disposable of a pen-sized device. In the currently envisioned improved use of this kind of device, the disposable strip placed in the device is replaced with a material wetted with glucose which has been drawn through the skin iontophoretically (without drawing blood). The sampling matrix is made of polyvinyl chloride, as is the disposable strip, or it may be made of some other material with better characteristics for iontophoretic sampling. The loading of the designated matrix is done as a separate step or, preferably, as part of an assay with simultaneous or concerted sampling and detection of glucose. The matrix for detection may be a disposable strip, as in the current detection system for blood, and used only once, or it may be a material which allows multiple sampling. The latter matrix may remain in place indefinitely or it may only be useful over a set time (number of assays). Preferably, it will be in proper juxtaposition with the electrode to allow the concerted assay. However, it is configured with the device (monitoring system) with respect to sampling and detection, the moistened matrix containing iontophoretically drawn glucose is applied over the accessible electrode area at the free end of the electrode. Here glucose oxidase catalyzes oxidation of the glucose, with the electrons generated being transferred to the underlying electrode via a mediator. The magnitude of the current generated is proportional to the blood glucose concentration in the sample and is displayed in mg/dL on the liquid crystal display built within the monitor. As they become commercially available, other comparably or even more sensitive means of detecting glucose may be substituted for the above described, commercially available blood sampling system.

Delivery-In-Vitro

The in-vitro delivery of a substance to a membrane of the present invention will also utilize FIGS. 1, 2, 3, 4 and 5. FIG. 6 shows for reference the state-of-the-art in vitro delivery system 60. The horizontal electrodes 61A and 61B combine on vertical membrane 62. The receptor liquid 63 originally will not contain any of the substance in liquid 64. When the circuit 65 is completed with power supply 66, the substance in 64 moves into and through membrane 62 and will appear in receptor liquid 63.

The equipment and technique for delivery in the present invention is similar to that described above for the in-vitro sampling. Any conductive material such as metals (platinum, aluminum, etc.), conductive gels (e.g. with sodium chloride solution, etc., conductive Solutions (sodium chloride in water, etc.) or any combination of these materials.

The permeable electrodes of the present invention range in size from about 1 $\mu m^2$ to 400 $cm^2$, preferably about 1 $mm^2$ to 40 $cm^2$. The current density is about 0.01 $\mu A/cm^2$ to 2 $mA/cm^2$, preferably 1 $\mu A/cm^2$ to 0.5 $mA/cm^2$. The electrodes may be attached by straps, adhesive, bands and the like.

The same membranes as described in in vitro sampling are pertinent here, e.g., full thickness or split thickness, skin, mucosal membranes, artificial polymer membranes and the like.

Sampling-In-Vivo

The figures useful in illustrating in vivo sampling are numbers 5, 7, 8, 9A and 9B. The information found above for in vitro sampling can be adapted and applied here.

In FIG. 7 is shown one embodiment of the sampling. The exterior of top cell 81 looks,very similar to top half 11 but has the shape of top 81. The electrodes appear to be similar or identical chambers 16A, 16B and 16C. Top 81 is attached using straps 82 to the living mammal 86 (human being). When electrode wires 26A and 26B are attached to power supply 83 via lines 84 and 84A a circuit is completed and sampling of the substance is collected in electrically conducting gel 25A or 25B. The main difference between top half 11 and top 81 is that the glass walls 15A and 15B, etc. extend to form a good seal on the horizontal membrane substrate at contact surface 85. (Power supply 83 may be small-watch size and portable).

It is known that drugs or their metabolites, such as alcohol, aminopyrine, methylurea, acetamide, sulfauanidine, sulfadiazine, theophylline, and other low molecular weight nonelectrolytes are secreted through the skin or mucous membrane in sweat, saliva or the like. Other compounds or their matablites which may be indicative of certain normal or disease conditions such as phenyalanine (phenylketonuria), sugar (diabetes) estriol (pregnancy) calcium (neoplasms) and copper (leukemia) for example, as well as normal and abnormal metabolites of other substances may be secreted in such fluids. Fluid collection is also used experimentally for determining biological requirements of various substances such as magnesium. If fluid samples are obtained and analyzed for these materials, the presence of such materials in the body can be detected. Such fluid collection therefore is useful in a wide variety of experimental, diagnostic, therapeutic and forensic medical purposes. While such fluids can be collected in numerous ways, the present invention describes a method of collection using a electrical current.

Additional compounds of interest are found for sampling or delivery to a human being in "Iontophoretic Devices for Drug Delivery," by Praveen Tyle, Pharmaceutical Research, Vol. 3, #6, pp. 318–326. Specific substances of interest for sampling as an ionic or a nonionic species is found on page 320 and is included below as Table 4.

TABLE 4

Substances of Interest for Delivery or Sampling

| DRUG | CONDITION/DISEASE | REFERENCE NO. |
|---|---|---|
| 1. Methylene blue and potassium iodide | Skin Disorders | Jenknson and Waiton(7)[a] |
| 2. Pencillin | Burns | Rapperport, et al. (10)[d] |
| 3. Histamine | Disease conditions of soft tissues, burses and tendons | Kling and Sahin (11)[a] |
| 4. Sodium iodide | Electrolytes | Strohl, et al. (15)[d] |
| 5. Sulfa drugs | Pycocyanus Infection | von Sallmann (16)[d] |
| 6. Dexmethasone, sodium phosphate, xylocaine | Musculoskeletal inflammatory conditions | Harris (17)[a] Delacerda (18)[a] |
| 7. Copper | Contraception | Riar, et al.(19)[d] |
| 8. Insulin | Diabetes | Karl(21)[d] Stephen, et al.(22)[d] |
| 9. Pilocarpine | Cystic fibrosis | Webster(23)[d] |
| 10. Ragweed pollen extract | Hay fever | Abramson(31)[a] |
| 11. Phosphorus | | O'Malley and Cester(35)[d] |
| 12. Water | Hyperhidrosis | Tapper(43)[a] |
| 13. Citrate | Rheumatoid arthritis | Coyer(51)[a] |
| 14. Dexamethasone Na phos & lidocaine HCl | Primary tendonitis | Bertolucci (52)[b] |
| 15. Hyaluronidase | Hemorrhages | Boone (53)[a] |
| 16. Vidarabine monophos. (Ara-AMP) | Keratitis (herpes virus) | Kwon et al. (54)[d] Hill et al. (56)[d] |
| 17. Lignocaine HCl or lidocaine | Topical analgesia | Comeau et al. (9, 28)[d] Russo et al. (12)[b] Echols et al. (27)[a] Siddiqui et al. (38)[c] Petelenz et al. (55)[b] Schleuning et al. (59)[c] Gangarosa (60, 61)[a] Arvidsson et al.(62)[a] |
| 18. Acetyl beta methylcholine Cl | Arteriosclerosis | Cohn and Benson (57)[a] |
| 19. Acetyl beta methylcholine | Arthritis | Martin et al.(58)[a] |
| 20. Idoxuridine | Herpes simplex keratis | Gangarosa et al.(60, 63)[b] |
| 21. Sodium floride | Dentin | Gangrosa (60)[a] |
| 22. Methylprednisolone succinate | Postherpetic neuralgia | Gangarosa et al.(64)[b] |
| 23. Lidocaine, epinephrine, and corticosteroid | Temporomandibular joint-myofascial pain dysfunction syndrome | Gangarosa and Mahan(65)[a] |
| 24. Sodium salicylate | Planter warts | Gordon and Weinstein (66)[a] |
| 25. Calcium | Myopathy | Kahn(67)[a] |
| 26. Acetic acid | Calcium deposits | Kahn(68)[a] |
| 27. Zinc | Nasal disorders | Weir(69)[a] |
| 28. Esterified glucocorticoids | Peyronic's disease | Rothfeld and Murray(70)[a] |
| 29. Vasopressin | Lateral septal neuron activity | Marchand and Hagino (71)[c] |
| 30. Alkaloids | Chronic pain | Csillik et al. (73)[a] |
| 31. Optidase | Arthrosis | Ulrich(74)[a] |
| 32. Natrium salicylicum butazolindin | Acute thrombophlebitis | Kostadinov et al. (75)[c] |
| 33. Penicillin | Pneumonia and abscesses of lungs | Sokolov et al. (76)[d] |
| 34. Paverine and nicotinic acid | Cervical osteochondrosis with neurological symptoms | Ostrokhovich and Strelkova (77)[d] |
| 35. Grasses | Allergy | Shilkrat(80)[a] |
| 36. 6-Hydroxydopamine | Ocular infection | Caudil et al.(81)[d] |
| 37. Metoprolol | Beta-blocker (angina pectoris) | Okabe et al. (82)[d] |

[a] Based on clinical impressions (qualitative)
[b] Based on double-blind study (well-controll study).
[c] Based on in vitro experiments.
[d] Based on controlled comparative study (quantitative, but not double blind).

Delivery-In-Vivo

The same type of device as shown in FIGS. 7, 8, 9A, 9B and 10 for sampling in vivo can be used for the in vivo delivery.

Biosensing Using Iontophoresis

In this aspect FIGS. 5, 7, 8, 9A and 9B are of importance. The description above for in vivo sampling is of interest plus an analyzing component.

The analyzing component may be (ion) specific electrodes, selective electrodes, electronic biosensors that connect specific biochemical changes to electric signals, colorimetric reagents and the like.

The indication of the presence of the substance of interest in the tissue of the patient may be qualitative or quantitative. The measured value may be linked to a drug delivery unit to provide an additional level of a therapeutic agent.

The sampling of the component may be by a single sampling iontophoresis electrode.

The analytical method when it senses that the substance (or bioactive material) in question has changed may automatically administer an appropriate level of need therapeutic agent. The measurement may also simply alert an operator that therapeutic agent needs to be added orally, dermally, rectally, buccally, intravenously or the like.

Advantages of the In-Vivo or In-Vitro Iontophoretic Sampling or Delivery

1. The sampling approach outlined herein is a simple, convenient and painless technique for sampling bioactive materials with the purpose of diagnosis or monitoring. Sampling can be continuous or periodic.

2. The sampling is highly significant in situations where a routine blood sample could not be drawn, or where acquisition of multiple blood samples is undesirable (e.g. from an infant).

3. The sampling technique offers characteristics that may ultimately be engineered into a "biofeedback" loop-type system. In other words, the iontophoretic device, while permitting sampling by the method described, can also be used to deliver a therapeutic agent by any administration route (i.e., in response to a need "sensed" by the sampling).

4. The sampling will make outpatient monitoring safe and simple and provide a use of iontophoresis of wide and rather general applicability.

5. The sampling or delivery of any bioative material can be modified if the sampled biomaterial does not cross the skin sufficiently rapidly: agents (e.g. alcohols, fatty acids, glycols, Azone, etc.) which lower the local barrier function of skin can be incorporated into the electrode device to improve the extraction or delivery flux.

6. The technique is amenable to sampling under both electrodes, i.e. to the simultaneous determination of more than a single bioactive agent (e.g. a drug and a metabolite or conjugate of the drug).

7. The technique as indicated, would not be solely limited to biomaterial sensing across the skin. Other mucosal surfaces are also suitable for the approach. Examples include the nasal mucosa, the rectum, the vagina and the inside of the mouth. These surfaces are presently used as sampling sites with varying degrees of success. Since these mucosal surfaces are, in general, well perfused by small blood vessels, and because these membranes are less resistive to molecular transport, small current applied for shorter times can be used when sampling from these tissues.

8. The technique has an efficiency which depends upon the current applied between the electrodes and the duration of current flow. These variables can be precisely controlled enabling reproducible sampling and permitting, thereby, the generation of reliable data for comparative purposes (e.g. contrasting the levels of a particular bioactive material before, during and after a therapeutic treatment). This would be a conspicuous advantage when sampling from the nose, a notoriously difficult site from which to obtain reproducible information.

9. Bioactive materials or substances which are charged or uncharged are candidates for iontophoretic administration or sampling. These include small protein, di- to polypeptides, lipophobic and lipophilic materials. Charged materials which often cannot be administered easily by other routes are preferred. See substances in U.S. Pat. Nos. 3,731,683 and 3,797,494, which are incorporated herein by reference.

10. The device makes it possible to sample or administer in vivo or in vitro a substances (or bioactive material) wherein the electrodes are on the same side of the subject surface. The sample is generally in a horizontal configuration while the electrode materials are adjacent to each other and in a generally vertical orientation. If the top of the device is sealed, it can be at any degree of orientation on the skin so long as electrical contact with the membrane surface is not impaired.

11. This device and technique makes it possible to sample or deliver drugs both systemically or locally. For instance, it is possible to use this technique to treat a skin cancer with methotrexate administered through the skin.

The following Examples are to be read as being illustrative and exemplary only. They are not to be construed as being limiting in any way.

EXAMPLE 1

IN VITRO SAMPLING

Testing of the Modeling Cell: Glass diffusion cells as described above (see FIGS. 1, 2, 3 or 4) were made by Skin Permeation Systems (L. G. A., Berkeley, Calif.). The cell 10 is a modification of a standard flow-through diffusion cell (LGA skin penetration cell catalog no. LG 1084-MPC), described by Gummer et al., *International Journal of Pharmacology*, Vol. 40, p. 101 ff, published in 1987.

The top half of the cell is divided into three compartments or chambers (16A, 16B or 16C) by two walls 15A and 15B so that the only physical/electrical connection between the two electrode chambers (16A and 16C in FIGS. 1, 2, 3 or 4) decreases the possibility of leakage between them and makes it possible to investigate questions involving skin continuity. The top half of the cell 12 has a channel 18 or trough below this space that isolates the skin from the rest of the receptor phase. Filling this channel 18 with receptor fluid 19 during an experiment keeps the skin above it moist. The bottom half of the cell 12 also has ports 20A and 20B for the continuous flow of the receptor phase 17 and ports 21A and 21B for water jacket 21C circulation. Capillarity between the compartment walls and the external well was prevented by silanizing the top of the cell with dichlorodimethyl silane (Aldrich Chemical Co., Milwaukee, Wis.). The cells used with a three-station magnetic stirrer unit and stirring bar 27. (LG-1083-MS, LGA, Berkeley).

Metal Electrodes Wires (26A and 26B)—Platinum wire (Pt wire—Fisher #B-766-5A, 99.95% pure).

Power Supply (29)—Current or voltage control with automatic crossover (Model APH 1000M, Kepco, Inc., Flushing, N.Y.). This supply has a specified drift of $\geq 2$ µA/8 hrs for its current-controlled output, an important consideration if drug flux is sensitive to changes in current.

Receptor Fluid (17)—Phosphate buffered saline (pH=7.4, 0.9% NaCl W/V).

Dye—Blue dye #1 FD&C in deionized water.

Drugs—Clonidine HCl (Sigma Chemical Co., St. Louis, Mo.); Clonidine-HCl (phenyl-4-$^3$H) of specific activity 90 mCi/mg (Amersham, Arlington Heights, Ill.). Morphine sulfate (Sigma Chemical Co., St. Louis, Mo.); Morphine (N-methyl-$^3$H) of specific activity 255 mCi/mg (New England Nuclear, Boston, Mass.). The non-labelled drugs were dissolved in deionized water to form solutions of 1 mg/ml, with enough labelled drug to achieve an activity of approximately 1 μCi/ml.

Skin (13)—Full-thickness skin, freshly excised from 11–15 week old female hairless mice (strain Skh:HR-1, Simonsen Laboratory, Gilroy, Calif.).

Testing of the Modeling Cell—The diffusion cell 10 was tested in three ways:

(1) Leakage tests (without current) using dye and silicone rubber than skin; (2) leakage tests using dye and skin (without current); and (3) iontophoretic tests using the drug solutions and skin (with and without current). Procedures (1) and (2) were evaluated by visually inspecting the cell. For procedure (3), 0.6 ml. of labelled drug solution was placed in chamber 16A, 0.6 ml of buffered saline was pipetted into chamber 16C, and a constant current of 0.63 mA/cm$^2$ (with the voltage limited at 9 V) was imposed between the electrodes in the two chambers. The activity of the solutions in chambers 16A and 16C was determined before and after iontophoresis. The activity of the skin 13 and of the samples taken from the receptor chamber was determined post-experimentally. Each experiment lasts approximately 24 hours, ±2 hours, with samples collected hourly. Receptor fluid 17 was magnetically stirred (27), and the collection flow rate was 10 ml/hr. Each procedure was repeated three times.

RESULTS

Procedures (1) and (2): No dye leakage was observed from the side chambers 16A and 16C to the middle chamber 16B, or from any chamber to the outside of the cell, for both the model silicone rubber membrane and the hairless mouse skin.

Procedure (3): When the dye in chamber 16A was replaced with a labelled drug and no current was applied, the drugs diffused into the receptor phase 17 with mean rates of 0.05 μg/cm$^2$/hr clonidine-HCl and 0.04 μg/cm$^2$/hr for morphine sulfate. In both cases, no drug was found in the buffered saline of chamber 16C after 20 hours.

When current was applied between the chamber with the labelled drug and the chamber with the buffered saline, permeation increased substantially. The rate of penetration of morphine sulfate through the skin with a current of 0.63 mA/cm$^2$ was 2.0 μg/cm$^2$/hr compared to the passive transport rate of 0.04 μg/cm$^2$/hr. In the case of clonidine-HCl, the rate changed from 0.05 μg/cm$^2$/hr without current to 15.0 μg/cm$^2$/hr with an electrical driving force. Labelled drug was detected in the buffered saline of chamber 16C, with 1 μg of morphine sulfate present approximately 20 hours (see FIG. 14), and 5 μg of clonidine after the same time.

The labelled drug might have entered chamber 16C by several paths, the most likely being that it was "pulled" back up through the skin under the passive electrode. To test this possibility, two cells were connected by tube 95 so that their receptor phases 92 and 93 were common but such that the skin and cell tops were physically separated (see FIG. 10). Labelled drug and the positive electrode were positioned in chamber 91A of cell 90A. The negative electrode was placed into chamber 91B in cell 90B. All other chambers (91C, 91D, 92 and 93) were filled with buffered saline. The remaining experimental procedures (electrical parameters, sampling were identical to those of Procedure 3 above). Labelled drug was transported into chamber 91A of cell 90A when the cells were connected in this fashion, demonstrating the existence of a "reverse transdermal" path in iontophoresis, which is in fact sampling by iontophoresis.

(b) Additional materials which are expected to be sampled in a similar manner as described hereinabove for clonidine include for example, morphine, heroin, insulin, neomycin, nitrofurasone, and beta-methasone.

EXAMPLE 2

IONTOPHORETIC SAMPLING IN VITRO

Iontophoretic sampling consists of pulling out chemical substances from the body through the skin by means of electricity. In order to test this method, an iontophoretic in-vitro cell is used (FIGS. 1, 2, 3 or 4). Full-thickness hairless mouse skin 13 (8–13 weeks old) is placed between the two parts of the cell. Solutions of radiolabelled drugs of known concentration in phosphate-buffered saline are circulated 10 ml/hr. beneath the skin. On top of the skin there are two self-adhesive gel electrodes, connected to a power supply which is set up in constant current mode (0.5 mA). Current is applied for measured length of time (about 2 hr.) corresponding to about 0.63 mA/cm$^2$. After the experiment the gel electrodes are taken for scintillation counting, which reflects the amount of drug absorbed by the gel electrodes. Using different drug concentrations with the same electrical current for the same period of time, a linear correlation between the amount is collected by the electrode and drug concentration is expected.

Results of the above described method using clonidine and theophylline in various concentrations are given in the graphs (FIGS. 11 and 12), each data point is a mean of at least two experiments. The graphic presentation of the data shows the linearity of the results.

IN-VITRO DELIVERY (a) Morphine—The procedures and conditions described for in vitro sampling were used for delivery of morphine: Current 0.63 mA/cm$^2$ for 20 hrs. using the cell described in FIGS. 1, 2, 3 or 4. The morphine was placed in Chamber 16A. After iontophoresis, morphine was found in chamber 16C. (See FIG. 14).

The electrically conducting gel for all experiments was KENZ-GEL-ELC gel of Nitto Electric Industrial Electric Company, Osaka, Japan.

(b) P.S.O.S. (Potassium Sucrose Octa Sulfate) P.S.O.S., 0.6 ml of 1.5 mg/ml solution in a boric buffer is placed in chamber 16A and boric acid buffer alone is placed in chamber 16C of FIGS. 1, 2 or 3. Using a direct current of 0.5 mA (0.65 mA/cm$^2$) transport of P.S.O.S. is observed up to 5 μg/hr. Using the same experimental configuration with a current only a few nanograms of P.S.O.S. was transferred. See FIG. 15.

IN-VIVO SAMPLING

The procedure and description above for in vitro sampling is used except that the membrane is replaced by the top of the forearm of a 29 year old male human being. The sampling cell used is the one in FIGS. 7, 8, 9A and 9B. The amount of clonidine sampled is comparable to that observed in the in vitro case.

IN-VIVO DELIVERY

FIG. 13 shows a diagram of a guinea pig having separate patch electrodes for sampling of bioactive materials from the mammal.

In order to examine the invention in vivo one test has been conducted so far. An iontophoretic procedure is applied on hairless guinea pig 133. One gel electrode 132(+) on line 131 with theophylline (5.5 μg, 2.4×4.2 cm) is placed on one side of the animal's back and another gel electrode 132A(−) on line 131A is attached to the other side of the back (separation distance approx. 7 cm). After 20 minutes at 1.0 mA (power supply 130), the gel electrodes are removed and 1.83 ng of theophylline is found in the negative electrode. The amount that is absorbed by the body of the guinea pig is 1.9 μg.

BIOSENSING USING IONTOPHORESIS

The sampling Of the radioactive clonidine in vitro is described above. When that procedure is adapted for in vivo sampling in a dog, the level of radioactive clonidine is measured iontophoretically, quickly and accurately. The operator is alerted when to administer an injection clondine to maintain the desired level of clonidine in the test dog.

MATERIALS AND METHODS

All of the following sampling experiments carried out below employ a cell (LG 1088-IC, Laboratory Glass Apparatus, Inc., Berkeley, Calif.) which allows the positioning of electrodes in physical and electrical isolation. The electrodes are also placed on the same side of the skin to mimic an in vivo iontophoretic sampling and/or delivery system.

Electrodes: Ag/AgCl electrodes are chosen as the current driving system due to their non-polarizable properties. They pass very large currents without changing the pH of the system or requiring a large input of energy. Pure silver wire (1 mm, 4 cm long, 99.999% pure, from Aldrich Chemical Co., Milwaukee, Wis.) was first cleaned with fine emery cloth and one end is manipulated into a small loop. The latter is then coated by dipping it into molten silver chloride (99.99% pure, from Aldrich Chemical Co., Milwaukee, Wis.). After cooling the noncoated silver wire is protected from contact with the electrolyte by shrink-to-fit, salt resistant, insulating tubing (1/16-in. internal diameter, irradiated, flexible polyolefin, from ICO Rally, Palo Alto, Calif. 94303). The electrode to be used as the anode in the iontophoresis experiment is then "cathodized" by making it the cathode and a platinum wire the anode. This step is done to ensure that there was sufficient silver metal in the electrode, when it acts as an anode, to allow the reaction:

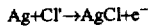

Electrolyte: The solution surrounding the anode and cathode contains N-2-hydroxyethylpiperazine-N'-2-ethanesuphonic acid (HEPES)-buffered saline ([Na$^+$]=147 mM, [Cl$^-$]=133 mM), adjusted to pH 7.4. The solution perfusing the dermal surface of the skin consisted of the same buffer and glucose (Sigma Chemical Company, St. Louis, Mo.) at a concentration of 6 mM, unless otherwise stated. Radiolabelled glucose, U-$^{14}$C, (ICN Biomedicals, Inc., Costa Mesa, Calif. Specific activity (1 mCi/mL) is added to produce a solution with an activity of 0.4 μCi/ml. The purity of the radiochemical is tested using thin-layer chromatography (TLC), and it is found that a purity level of greater than 99% existed.

Skin Sources: All experiments used full thickness skin from female hairless mice (HRS/hr, Simonsen Laboratories, Gilroy, Calif.) that were 8–15 weeks old. The skin is removed from the animals at sacrifice and is used immediately.

Current Delivery: Iontophoresis was performed under constant current conditions (0.36 mA/cm$^2$). The current was delivered from a power supply (Built and available from John L. Cahoon, Professional Design and Development Services, U.C. Berkeley, Calif.), which had been interfaced with a computer (Macintosh IIfx, Apple Computer, Inc.) using a commercial software package: "LabVIEW" (National Instruments Corporation, Austin, Tex.).

Iontophoretic Sampling Determination: The diffusion cell is assembled with the hairless mouse skin separating the electrode compartment and the compartment containing radioactive glucose. A one cm$^3$ volume of buffer-saline solution is used to bathe both electrodes. A current of 0.4 mA (equivalent to a current density of 0.36 mA/cm$^2$), is then passed for 2 hours unless otherwise stated.

After the 2 hour period 0.5 cm$^3$ aliquots are removed from the electrode compartments and the amount of radioactivity is determined by liquid scintillation. The concentration of the glucose in each of these two compartments is calculated by comparing their radioactivity of the glucose solution bathing the dermal side of the side. Passive transport of glucose is also measured by following an identical protocol, but using no current.

Results: The results obtained are shown in FIGS. 16–20. Each Figure has a separate description below having pertinent experimental details.

A neutral molecule, such as glucose should, in theory, be transported preferentially to the cathodal chamber due to the skin's permselectivity. These experimental results, however, show a surprisingly higher amount of radioactivity in the anodal chamber. Solvent flow data, using tritiated water, shows that the electroosmotic flow of solvent is major driving force for transdermal transport of the radiolabel is direct electrostatic repulsion. This transport can happen if the glucose, upon entering the skin is metabolized to form negatively charged ions, which are then attracted to the anode.

Analysis of the aliquots using High Performance Liquid Chromatography (HPLC), indicates that metabolism is indeed occurring: Preliminary results show that 87% of the compound in the cathodal chamber is glucose, whereas only 23% of extracted material in the anodal chamber is parent glucose.

The glucose system is then investigated further to observe the kinetics of the extraction process, the linearity of the system (i.e. sampling as a function of dermal side glucose concentration) and the reproducibility.

Biosensor: A biosensor which measures the low concentration of substance, e.g. glucose or the higher concentration of metabolite is needed. Some biosensors are conventional in the art. The question of whether there is a single metabolite or a mixture and the identity of the metabolite is apparent.

At present, therefore, there is a need for a very sensitive, non-selective biosensor. The non-selectivity of the biosensor would allow one to measure the higher metabolite concentration. The blood glucose concentration level is thus measured from its metabolite concentration.

An electrochemical sensor which exploits the existence of an unstable copper state is used in HPLC to measure very low concentrations of reducing and non-reducing sugars. The electrode however only functions at very high pH. It is anticipated that such an electrode can be developed to suit the iontophoresis cell conditions.

The system can, theoretically, be used to detect blood concentrations of other molecules. These molecules can either be naturally occurring or drugs that have been administered to the body. Both charged and neutral molecules are sampled; the electroosmotic flow is exploited for the latter case.

The sampling device will therefore be a very flexible system which can be exploited in a number of different applications. Environmental monitoring of charged pesticides or metabolites is an immediate choice. The noninvasive property of the device also allows the system to be a neonatal application, where invasive techniques of extraction are very difficult. In these systems, however, a sensor with sufficient sensitivity is a prerequisite.

The iontophoretic system has an inherent advantage over other diagnostic techniques in that the molecule, whose concentration is to be measured, is extracted into both anodal and cathodal chambers. It is possible, therefore, to obtain two concentration measurements independently for each experiment. This will enhance the reliability of the sampling device.

Preliminary experiments have been carried out measuring the iontophoretic sampling of ethanol in a membrane of a mammal. The ethanol molecule does not seem to be metabolized as the cathodal concentration is greater than anodal as is predicted by theory.

A final biosensor to be used in the iontophoretic device must fulfill the following criteria:

(1) High sensitivity. The sensor measures small concentration of glucose or associated metabolites;
(2) The response time of the sensor is kept to a minimum;
(3) The sensor is selective to either the glucose or its metabolites;
(4) The sensor is economically priced.

Of all contemporary sensors, an electrochemical system seems to be the best choice.

A copper chemically modified electrode (Cu—CME) is used in HPLC analysis. At a potential of 0.45V and high pH, an unstable oxidation state of copper exists. This electrode allows direct oxidation and hence detection of reducing sugars and non-reducing sugars at the picomole levels. The absence of a mediator also confers a long lifetime on the system.

The enzyme glucose oxidase can be immobilized on a platinum electrode. The enzyme reacts with glucose and oxygen to produce hydrogen peroxide, which can be oxidized on the platinum electrode. The sensitivity of this electrode is, however, at a lower level than that of the copper modified electrode.

FIG. 16 shows a graph of the iontophoretic device results obtained from ten different mice for glucose. The passive flux was negligible and is not shown in the figure.

A current of 0.4 mA (=0.36 mA/cm2) was passed for two hours at pH 7.4.

Note of high anodal concentration in comparison with the cathodal concentration. Theory predicts an opposite trend.

FIG. 17 is a graphic summary of iontophoretic experiments to show the skin is indeed permselective for sodium ions the solvent flow during iontophoresis.

Tritiated water (Biotechnology Department, Dupont, Wilmington, Del.) was used to 'spike' the dermal side solution. Glucose at a concentration of 5 mM was also present in the dermal side solution. Aliquots were removed after a two hour period and the radioactivity was measured using liquid scintillation. 0.4 uCi/mL was used.

The results of FIG. 17 show that there is a greater flux to the cathode over the anodal flux.

FIG. 18 shows a graphic representation of the iontophoretic experimental results show how reproducible iontophoretic sampling is on the same piece of skin and if the sampling is linear as a function of dermal side glucose concentration (See FIGS. 18A and 18B).

The results of FIG. 16 which indicate a large variation in amount of glucose extracted with different pieces of skin.

One mouse was slaughtered to produce sufficient skin for two cells. Iontophoretic sampling was then carried out under the following conditions:

| Experiment Number | Cell a | Cell b |
|---|---|---|
| 1 | 1 mM | 100 mM |
| 2 | 5 mM | 50 mM |
| 3 | 50 mM | 5 mM |
| 4 | 100 mM | 1 mM |

Thus the importance of current damage and experimental error will be seen in the results.

From FIGS. 18, 18A and 18B it is seen that iontophoretic sampling is a reproducible phenomenon when the skin originates from the same animal.

FIG. 19—The time necessary for the glucose to be transported through the skin is an important factor. To observe the kinetics of this transport an experiment was carried out on 4 cells and current was passed for 30 minute intervals. After each interval 0.5 mL aliquots were removed and the radioactivity measured. The results are shown graphically in FIG. 19.

Transport to the anode appears to reach a steady state magnitude after only half an hour. Cathodal transport even after 2 hours is still pre-steady state. This is indicative of a faster flux to the anode and implies that the transporting species are most likely charged.

FIG. 5—The iontophoretic sampling was extended to another neutral bioactive molecule: ethanol. An identical protocol to that employed for glucose experiments is followed. The only difference being in the concentration of ethanol in the dermal side. A concentration of 17 mM was used as this corresponds to a 0.08% solution, the maximum blood alcohol level legally allowed.

Radioactivity was again used to measure the extracted ethanol. The dermal side using radioactive ethanol, [1–14C] (Amersham Co., Arlington, Ill.) had an activity of 0.4 uCi/mL.

It is an immediately apparent and surprising result that there is a large passive flux. Further, the amount of ethanol extracted iontophoretically is far greater than that obtained with glucose, even when taking into account the greater ethanol concentration on the dermal side.

While only a few embodiments of the invention have been shown and described herein, it will become apparent to those skilled in the art that various modifications and changes can be made in the iontophoresis diffusion cell for in-vitro and in-vivo sampling of bioactive molecules and for the in-vitro and in-vivo delivery of bioactive molecules or in biosensing applications without departing from the spirit and scope of the present invention. All such modifications and changes coming within the scope of the appended claims are intended to be carried out thereby.

We claim:

1. An iontophoretic method for the substantially continuously in vivo monitoring of blood glucose in a mammal, the method comprising the steps of:
   (a) placing a device comprised of a first electrically conducting means, a second electrically conducting means, and at least one collection reservoir on the skin or mucous membrane of the mammal to be monitored, wherein said second electrically conducting means is physically and electrically separated from said first electrically conducting means,
   (b) connecting said device to an electrical source to create an electrical circuit, (c) continuously applying a constant current in said electrical circuit to cause said blood glucose to migrate into said collection reservoir, and (d) collecting and monitoring the glucose in said collection reservoir, with the proviso that the contact of the device on the skin or mucous membrane and the collection occurs at physiologically acceptable pH conditions.

2. The method of claim 1 additionally comprising the step of correlating the collected glucose to a glucose blood concentration.

3. The method of claim 1 wherein step (d) is accomplished using at least one analyzing device selected from the group consisting of a glucose or glucose metabolite biosensor, a glucose or glucose metabolite selective electrode, and a glucose or glucose metabolite specific colorimetric reagent, wherein said analyzing device is located in said collection reservoir.

4. The method of claim 3 wherein said analyzing device is linked to a glucose delivery device and the method further includes step (e) delivery of glucose to the mammal in need of glucose.

5. The method of claim 3 wherein said analyzing device is linked to an alarm system to alert an operator that the monitored mammal requires additional glucose.

6. A method of monitoring glucose transferred from a source within mammalian tissue, the method comprising the following steps:

placing a glucose collector against the mammalian tissue surface;

substantially continuously transferring glucose from the source into the glucose collector; and monitoring the glucose within the glucose collector, with the proviso that contact of the glucose collector with the tissue surface and the collection occur under physiologically acceptable pH conditions.

7. The method of claim 6 wherein the glucose collector uses a reservoir.

8. The method of claim 6 wherein the mammalian tissue is human skin.

9. The method of claim 8 wherein the method is performed in vivo.

10. The method of claim 6 wherein the transferring step uses iontophoresis.

11. The method of claim 10 further comprising the step of first placing an electrode against the mammalian tissue surface.

12. The method of claim 10 wherein the mammalian tissue is human skin.

13. The method of claim 12 wherein the method is performed in vivo.

14. The method of claim 6 wherein the monitoring step comprises measuring the concentration of glucose within the glucose collector.

15. A method of monitoring glucose metabolite transferred from a source across mammalian tissue, the method comprising the following steps:

placing a glucose metabolite collector against a tissue surface;

substantially continuously transferring glucose metabolite from the source into the glucose metabolite collector; and monitoring the glucose metabolite within the glucose metabolite collector, with the proviso that contact of the glucose metabolite collector with the tissue surface and the collection occur under physiologically acceptable pH conditions.

16. The method of claim 15 wherein the glucose metabolite collector comprises a reservoir.

17. The method of claim 15 wherein the mammalian tissue is human skin.

18. The method of claim 17 wherein the method is performed in vivo.

19. The method of claim 15 wherein the transferring step uses iontophoresis.

20. The method of claim 19 further comprising the step of first placing an electrode against the mammalian tissue surface.

21. The method of claim 19 wherein the mammalian tissue is human skin.

22. The method of claim 21 wherein the method is performed in vivo.

23. The method of claim 15 wherein the monitoring step includes measuring the concentration of glucose metabolite within the glucose metabolite collector.

* * * * *